US 8,112,292 B2

(12) United States Patent
Simon

(10) Patent No.: US 8,112,292 B2
(45) Date of Patent: Feb. 7, 2012

(54) METHOD AND APPARATUS FOR OPTIMIZING A THERAPY

(75) Inventor: David A. Simon, Boulder, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 1442 days.

(21) Appl. No.: 11/409,499

(22) Filed: Apr. 21, 2006

(65) Prior Publication Data

US 2007/0249911 A1 Oct. 25, 2007

(51) Int. Cl.
*G06Q 50/00* (2006.01)

(52) U.S. Cl. .......................................... 705/3; 128/898

(58) Field of Classification Search .................. 705/2–3; 128/898

See application file for complete search history.

(56) References Cited

U.S. PATENT DOCUMENTS

| | | |
|---|---|---|
| 1,576,781 A | 3/1926 | Phillips |
| 1,735,726 A | 11/1929 | Bornhardt |
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kähne et al. |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |

(Continued)

FOREIGN PATENT DOCUMENTS

CA 964149 3/1975

(Continued)

OTHER PUBLICATIONS

Finnis et al. ("Three-Dimensional Database of Subcortical Electrophysiology for Image-Guided Stereotactic Functional Neurosurgery", IEEE Transactions on Medical Imaging, 22 #1, Jan. 2003, pp. 93-104).*

(Continued)

*Primary Examiner* — Gerald J. O'Connor
*Assistant Examiner* — Mark Holcomb
(74) *Attorney, Agent, or Firm* — Harness, Dickey

(57) ABSTRACT

A method and apparatus to perform a procedure that can include a processor assisted surgical procedure. During the procedure patient space and image space can be registered to allow for tracking of various tracking sensors. An instrument can be placed relative to patient space based upon a plan.

48 Claims, 10 Drawing Sheets

U.S. PATENT DOCUMENTS

| | | |
|---|---|---|
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,403,321 A | 9/1983 | DiMarco |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,485,815 A | 12/1984 | Amplatz |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Bludermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Öberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,117,836 A | 6/1992 | Millar |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |

| Patent | Date | Inventor |
|---|---|---|
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Müller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,484,437 A | 1/1996 | Michelson |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,490,196 A | 2/1996 | Rudich et al. |
| 5,494,034 A | 2/1996 | Schlondorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,531,227 A | 7/1996 | Schneider |
| 5,531,520 A | 7/1996 | Grimson et al. |
| 5,531,673 A | 7/1996 | Helenowski |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,558,638 A | 9/1996 | Evers et al. |
| 5,566,681 A | 10/1996 | Manwaring et al. |
| 5,568,384 A | 10/1996 | Robb et al. |
| 5,568,809 A | 10/1996 | Ben-haim |
| 5,571,109 A | 11/1996 | Bertagnoli |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,583,758 A * | 12/1996 | McIlroy et al. .................. 705/2 |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |

| | | | | | | |
|---|---|---|---|---|---|---|
| 5,627,873 A | 5/1997 | Hanover et al. | | 5,823,958 A | 10/1998 | Truppe |
| 5,628,315 A | 5/1997 | Vilsmeier et al. | | 5,824,048 A | 10/1998 | Tuch |
| 5,630,431 A | 5/1997 | Taylor | | 5,828,725 A | 10/1998 | Levinson |
| 5,636,644 A | 6/1997 | Hart et al. | | 5,828,770 A | 10/1998 | Leis et al. |
| 5,638,819 A | 6/1997 | Manwaring et al. | | 5,829,444 A | 11/1998 | Ferre et al. |
| 5,640,170 A | 6/1997 | Anderson | | 5,831,260 A | 11/1998 | Hansen |
| 5,642,395 A | 6/1997 | Anderton et al. | | 5,833,608 A | 11/1998 | Acker |
| 5,643,268 A | 7/1997 | Vilsmeier et al. | | 5,834,759 A | 11/1998 | Glossop |
| 5,645,065 A | 7/1997 | Shapiro et al. | | 5,836,954 A | 11/1998 | Heilbrun et al. |
| 5,646,524 A | 7/1997 | Gilboa | | 5,840,024 A | 11/1998 | Taniguchi et al. |
| 5,647,361 A | 7/1997 | Damadian | | 5,840,025 A | 11/1998 | Ben-Haim |
| 5,662,111 A | 9/1997 | Cosman | | 5,843,076 A | 12/1998 | Webster, Jr. et al. |
| 5,664,001 A | 9/1997 | Tachibana et al. | | 5,848,967 A | 12/1998 | Cosman |
| 5,674,296 A | 10/1997 | Bryan et al. | | 5,851,183 A | 12/1998 | Bucholz |
| 5,676,673 A | 10/1997 | Ferre et al. | | 5,865,846 A | 2/1999 | Bryan et al. |
| 5,681,260 A | 10/1997 | Ueda et al. | | 5,868,674 A | 2/1999 | Glowinski et al. |
| 5,682,886 A | 11/1997 | Delp et al. | | 5,868,675 A | 2/1999 | Henrion et al. |
| 5,682,890 A | 11/1997 | Kormos et al. | | 5,871,445 A | 2/1999 | Bucholz |
| 5,690,108 A | 11/1997 | Chakeres | | 5,871,455 A | 2/1999 | Ueno |
| 5,690,117 A | 11/1997 | Gilbert | | 5,871,487 A | 2/1999 | Warner et al. |
| 5,694,945 A | 12/1997 | Ben-Haim | | 5,873,822 A | 2/1999 | Ferre et al. |
| 5,695,500 A | 12/1997 | Taylor et al. | | 5,882,304 A | 3/1999 | Ehnholm et al. |
| 5,695,501 A | 12/1997 | Carol et al. | | 5,884,410 A | 3/1999 | Prinz |
| 5,697,377 A | 12/1997 | Wittkampf | | 5,889,834 A | 3/1999 | Vilsmeier et al. |
| 5,702,406 A | 12/1997 | Vilsmeier et al. | | 5,891,034 A | 4/1999 | Bucholz |
| 5,711,299 A | 1/1998 | Manwaring et al. | | 5,891,157 A | 4/1999 | Day et al. |
| 5,713,946 A | 2/1998 | Ben-Haim | | 5,904,691 A | 5/1999 | Barnett et al. |
| 5,715,822 A | 2/1998 | Watkins et al. | | 5,907,395 A | 5/1999 | Schulz et al. |
| 5,715,836 A | 2/1998 | Kliegis et al. | | 5,913,820 A | 6/1999 | Bladen et al. |
| 5,718,241 A | 2/1998 | Ben-Haim et al. | | 5,920,395 A | 7/1999 | Schulz |
| 5,727,552 A | 3/1998 | Ryan | | 5,921,992 A | 7/1999 | Costales et al. |
| 5,727,553 A | 3/1998 | Saad | | 5,923,727 A | 7/1999 | Navab |
| 5,729,129 A | 3/1998 | Acker | | 5,928,248 A | 7/1999 | Acker |
| 5,730,129 A | 3/1998 | Darrow et al. | | 5,938,603 A | 8/1999 | Ponzi |
| 5,730,130 A | 3/1998 | Fitzpatrick et al. | | 5,938,694 A | 8/1999 | Jaraczewski et al. |
| 5,732,703 A | 3/1998 | Kalfas et al. | | 5,947,980 A | 9/1999 | Jensen et al. |
| 5,733,259 A | 3/1998 | Valcke et al. | | 5,947,981 A | 9/1999 | Cosman |
| 5,735,278 A | 4/1998 | Hoult et al. | | 5,950,629 A | 9/1999 | Taylor et al. |
| 5,735,814 A | 4/1998 | Elsberry et al. | | 5,951,475 A | 9/1999 | Gueziec et al. |
| 5,738,096 A | 4/1998 | Ben-Haim | | 5,951,571 A | 9/1999 | Audette |
| 5,740,802 A | 4/1998 | Nafis et al. | | 5,954,647 A | 9/1999 | Bova et al. |
| 5,740,808 A | 4/1998 | Panescu et al. | | 5,957,844 A | 9/1999 | Dekel et al. |
| 5,741,214 A | 4/1998 | Ouchi et al. | | 5,964,796 A | 10/1999 | Imran |
| 5,742,394 A | 4/1998 | Hansen | | 5,967,980 A | 10/1999 | Ferre et al. |
| 5,744,953 A | 4/1998 | Hansen | | 5,967,982 A | 10/1999 | Barnett |
| 5,748,767 A | 5/1998 | Raab | | 5,968,047 A | 10/1999 | Reed |
| 5,749,362 A | 5/1998 | Funda et al. | | 5,970,499 A * | 10/1999 | Smith et al. ........................ 1/1 |
| 5,749,835 A | 5/1998 | Glantz | | 5,971,997 A | 10/1999 | Guthrie et al. |
| 5,752,513 A | 5/1998 | Acker et al. | | 5,976,156 A | 11/1999 | Taylor et al. |
| 5,755,725 A | 5/1998 | Druais | | 5,980,535 A | 11/1999 | Barnett et al. |
| RE35,816 E | 6/1998 | Schulz | | 5,983,126 A | 11/1999 | Wittkampf |
| 5,758,667 A | 6/1998 | Slettenmark | | 5,987,349 A | 11/1999 | Schulz |
| 5,762,064 A | 6/1998 | Polyani | | 5,987,960 A | 11/1999 | Messner et al. |
| 5,767,669 A | 6/1998 | Hansen et al. | | 5,999,837 A | 12/1999 | Messner et al. |
| 5,767,960 A | 6/1998 | Orman | | 5,999,840 A | 12/1999 | Grimson et al. |
| 5,769,789 A | 6/1998 | Wang et al. | | 6,001,130 A | 12/1999 | Bryan et al. |
| 5,769,843 A | 6/1998 | Abela et al. | | 6,006,126 A | 12/1999 | Cosman |
| 5,769,861 A | 6/1998 | Vilsmeier | | 6,006,127 A | 12/1999 | Van Der Brug et al. |
| 5,772,594 A | 6/1998 | Barrick | | 6,013,087 A | 1/2000 | Adams et al. |
| 5,772,661 A | 6/1998 | Michelson | | 6,014,580 A | 1/2000 | Blume et al. |
| 5,775,322 A | 7/1998 | Silverstein et al. | | 6,016,439 A | 1/2000 | Acker |
| 5,776,064 A | 7/1998 | Kalfas et al. | | 6,019,725 A | 2/2000 | Vesely et al. |
| 5,782,765 A | 7/1998 | Jonkman | | 6,024,695 A | 2/2000 | Taylor et al. |
| 5,787,886 A | 8/1998 | Kelly et al. | | 6,026,316 A | 2/2000 | Kucharczyk et al. |
| 5,792,055 A | 8/1998 | McKinnon | | 6,050,724 A | 4/2000 | Schmitz et al. |
| 5,795,294 A | 8/1998 | Luber et al. | | 6,059,718 A | 5/2000 | Taniguchi et al. |
| 5,797,849 A | 8/1998 | Vesely et al. | | 6,063,022 A | 5/2000 | Ben-Haim |
| 5,799,055 A | 8/1998 | Peshkin et al. | | 6,064,904 A | 5/2000 | Yanof et al. |
| 5,799,099 A | 8/1998 | Wang et al. | | 6,071,288 A | 6/2000 | Carol et al. |
| 5,800,352 A | 9/1998 | Ferre et al. | | 6,073,043 A | 6/2000 | Schneider |
| 5,800,535 A | 9/1998 | Howard, III | | 6,076,008 A | 6/2000 | Bucholz |
| 5,802,719 A | 9/1998 | O'Farrell, Jr. et al. | | 6,096,050 A | 8/2000 | Audette |
| 5,803,089 A | 9/1998 | Ferre et al. | | 6,104,944 A | 8/2000 | Martinelli |
| 5,807,252 A | 9/1998 | Hassfeld et al. | | 6,118,845 A | 9/2000 | Simon et al. |
| 5,810,008 A | 9/1998 | Dekel et al. | | 6,122,538 A | 9/2000 | Sliwa, Jr. et al. |
| 5,810,728 A | 9/1998 | Kuhn | | 6,122,541 A | 9/2000 | Cosman et al. |
| 5,810,735 A | 9/1998 | Halperin et al. | | 6,131,396 A | 10/2000 | Duerr et al. |
| 5,820,553 A | 10/1998 | Hughes | | 6,139,183 A | 10/2000 | Graumann |
| 5,823,192 A | 10/1998 | Kalend et al. | | 6,147,480 A | 11/2000 | Osadchy et al. |

| | | | |
|---|---|---|---|
| 6,149,592 A | 11/2000 | Yanof et al. | |
| 6,156,067 A | 12/2000 | Bryan et al. | |
| 6,161,032 A | 12/2000 | Acker | |
| 6,165,181 A | 12/2000 | Heilbrun et al. | |
| 6,167,296 A | 12/2000 | Shahidi | |
| 6,172,499 B1 | 1/2001 | Ashe | |
| 6,175,756 B1 | 1/2001 | Ferre et al. | |
| 6,178,345 B1 | 1/2001 | Vilsmeier et al. | |
| 6,194,639 B1 | 2/2001 | Botella et al. | |
| 6,198,794 B1 | 3/2001 | Peshkin et al. | |
| 6,201,387 B1 | 3/2001 | Govari | |
| 6,201,988 B1 | 3/2001 | Bourland et al. | |
| 6,203,497 B1 | 3/2001 | Dekel et al. | |
| 6,206,885 B1 | 3/2001 | Ghahremani et al. | |
| 6,211,666 B1 | 4/2001 | Acker | |
| 6,223,067 B1 | 4/2001 | Vilsmeier et al. | |
| 6,233,476 B1 | 5/2001 | Strommer et al. | |
| 6,246,231 B1 | 6/2001 | Ashe | |
| 6,259,942 B1 | 7/2001 | Westermann et al. | |
| 6,273,896 B1 | 8/2001 | Franck et al. | |
| 6,283,951 B1 | 9/2001 | Flaherty et al. | |
| 6,285,902 B1 | 9/2001 | Kienzle, III et al. | |
| 6,298,262 B1 | 10/2001 | Franck et al. | |
| 6,314,310 B1 | 11/2001 | Ben-Haim et al. | |
| 6,332,089 B1 | 12/2001 | Acker et al. | |
| 6,341,231 B1 | 1/2002 | Ferre et al. | |
| 6,348,058 B1 | 2/2002 | Melkent et al. | |
| 6,351,659 B1 | 2/2002 | Vilsmeier | |
| 6,381,485 B1 | 4/2002 | Hunter et al. | |
| 6,385,483 B1 | 5/2002 | Uber, III et al. | |
| 6,390,097 B1 * | 5/2002 | Chandra | 128/898 |
| 6,402,689 B1 | 6/2002 | Scarantino et al. | |
| 6,406,426 B1 | 6/2002 | Reuss et al. | |
| 6,424,856 B1 | 7/2002 | Vilsmeier et al. | |
| 6,427,314 B1 | 8/2002 | Acker | |
| 6,428,547 B1 | 8/2002 | Vilsmeier et al. | |
| 6,434,415 B1 | 8/2002 | Foley et al. | |
| 6,437,567 B1 | 8/2002 | Schenck et al. | |
| 6,445,943 B1 | 9/2002 | Ferre et al. | |
| 6,464,662 B1 | 10/2002 | Raghavan et al. | |
| 6,470,207 B1 | 10/2002 | Simon et al. | |
| 6,474,341 B1 | 11/2002 | Hunter et al. | |
| 6,478,802 B2 | 11/2002 | Kienzle, III et al. | |
| 6,482,182 B1 | 11/2002 | Carroll et al. | |
| 6,484,049 B1 | 11/2002 | Seeley et al. | |
| 6,490,475 B1 | 12/2002 | Seeley et al. | |
| 6,491,699 B1 | 12/2002 | Henderson et al. | |
| 6,493,573 B1 | 12/2002 | Martinelli et al. | |
| 6,498,944 B1 | 12/2002 | Ben-Haim et al. | |
| 6,499,488 B1 | 12/2002 | Hunter et al. | |
| 6,516,046 B1 | 2/2003 | Fröhlich et al. | |
| 6,516,212 B1 | 2/2003 | Bladen et al. | |
| 6,526,415 B2 * | 2/2003 | Smith et al. | 1/1 |
| 6,527,443 B1 | 3/2003 | Vilsmeier et al. | |
| 6,531,152 B1 | 3/2003 | Lerner et al. | |
| 6,549,803 B1 | 4/2003 | Raghavan et al. | |
| 6,551,325 B2 | 4/2003 | Neubauer et al. | |
| 6,567,690 B2 | 5/2003 | Giller et al. | |
| 6,584,174 B2 | 6/2003 | Schubert et al. | |
| 6,609,022 B2 | 8/2003 | Vilsmeier et al. | |
| 6,611,700 B1 | 8/2003 | Vilsmeier et al. | |
| 6,640,128 B2 | 10/2003 | Vilsmeier et al. | |
| 6,658,396 B1 | 12/2003 | Tang et al. | |
| 6,671,538 B1 * | 12/2003 | Ehnholm et al. | 600/425 |
| 6,694,162 B2 | 2/2004 | Hartlep | |
| 6,701,179 B1 | 3/2004 | Martinelli et al. | |
| 6,740,883 B1 | 5/2004 | Stodilka et al. | |
| 6,755,789 B2 | 6/2004 | Stringer et al. | |
| 6,828,966 B1 | 12/2004 | Gavriliu et al. | |
| 6,901,287 B2 | 5/2005 | Davis et al. | |
| 6,905,492 B2 | 6/2005 | Zvuloni et al. | |
| 6,973,718 B2 | 12/2005 | Sheppard, Jr. et al. | |
| 6,979,348 B2 | 12/2005 | Sundar | |
| 6,982,282 B2 | 1/2006 | Lambert et al. | |
| 7,011,814 B2 | 3/2006 | Suddarth et al. | |
| 7,047,235 B2 | 5/2006 | Yang et al. | |
| 7,072,705 B2 | 7/2006 | Miga et al. | |
| 7,081,088 B2 | 7/2006 | Geiger | |
| 7,092,748 B2 | 8/2006 | Valdes Sosa et al. | |
| 7,103,399 B2 | 9/2006 | Miga et al. | |
| 7,167,180 B1 | 1/2007 | Shibolet | |
| 7,194,295 B2 | 3/2007 | Vilsmeier | |
| 7,313,430 B2 * | 12/2007 | Urquhart et al. | 600/429 |
| 7,599,730 B2 * | 10/2009 | Hunter et al. | 600/424 |
| 2001/0007918 A1 | 7/2001 | Vilsmeier et al. | |
| 2002/0095081 A1 | 7/2002 | Vilsmeier | |
| 2003/0078485 A1 | 4/2003 | Hartlep | |
| 2003/0101081 A1 * | 5/2003 | Putnam et al. | 705/4 |
| 2003/0114752 A1 | 6/2003 | Henderson et al. | |
| 2003/0191408 A1 | 10/2003 | Montgomery | |
| 2004/0024309 A1 | 2/2004 | Ferre et al. | |
| 2004/0039259 A1 * | 2/2004 | Krause et al. | 600/300 |
| 2004/0068172 A1 | 4/2004 | Nowinski et al. | |
| 2004/0092809 A1 | 5/2004 | DeCharms | |
| 2004/0097806 A1 * | 5/2004 | Hunter et al. | 600/434 |
| 2004/0107210 A1 | 6/2004 | Yang et al. | |
| 2004/0138551 A1 | 7/2004 | Hartlep et al. | |
| 2004/0158313 A1 | 8/2004 | Altman | |
| 2004/0210124 A1 | 10/2004 | Nowinski et al. | |
| 2004/0215071 A1 | 10/2004 | Frank et al. | |
| 2004/0215162 A1 | 10/2004 | Putz | |
| 2004/0236554 A1 | 11/2004 | Raghavan et al. | |
| 2004/0240753 A1 | 12/2004 | Hu et al. | |
| 2005/0002918 A1 | 1/2005 | Strauss et al. | |
| 2005/0004617 A1 | 1/2005 | Dawant et al. | |
| 2005/0018885 A1 | 1/2005 | Chen et al. | |
| 2005/0031210 A1 | 2/2005 | Shen et al. | |
| 2005/0049486 A1 * | 3/2005 | Urquhart et al. | 600/429 |
| 2005/0070781 A1 | 3/2005 | Dawant et al. | |
| 2005/0084146 A1 | 4/2005 | Watson et al. | |
| 2005/0085714 A1 | 4/2005 | Foley et al. | |
| 2005/0101855 A1 | 5/2005 | Miga et al. | |
| 2005/0111621 A1 | 5/2005 | Riker et al. | |
| 2005/0148859 A1 | 7/2005 | Miga et al. | |
| 2005/0171558 A1 | 8/2005 | Abovitz et al. | |
| 2005/0245814 A1 | 11/2005 | Anderson et al. | |
| 2006/0017749 A1 | 1/2006 | McIntyre et al. | |
| 2006/0084867 A1 | 4/2006 | Tremblay et al. | |
| 2006/0182321 A1 | 8/2006 | Hu et al. | |
| 2006/0217733 A1 | 9/2006 | Plassky et al. | |
| 2007/0021668 A1 | 1/2007 | Boese et al. | |
| 2007/0100226 A1 | 5/2007 | Yankelevitz et al. | |
| 2008/0081982 A1 | 4/2008 | Simon et al. | |

FOREIGN PATENT DOCUMENTS

| | | |
|---|---|---|
| DE | 3042343 A1 | 6/1982 |
| DE | 35 08 730 | 3/1985 |
| DE | 37 17 871 | 5/1987 |
| DE | 38 38 011 | 11/1988 |
| DE | 3831278 A1 | 3/1989 |
| DE | 42 13 426 | 4/1992 |
| DE | 42 25 112 | 7/1992 |
| DE | 4233978 C1 | 4/1994 |
| DE | 197 15 202 | 4/1997 |
| DE | 197 47 427 | 10/1997 |
| DE | 197 51 761 | 11/1997 |
| DE | 198 32 296 | 7/1998 |
| DE | 10085137 | 11/2002 |
| EP | 0 062 941 | 3/1982 |
| EP | 0 119 660 | 9/1984 |
| EP | 0 155 857 | 1/1985 |
| EP | 0319844 A1 | 1/1988 |
| EP | 0 326 768 | 12/1988 |
| EP | 0419729 A1 | 9/1989 |
| EP | 0350996 A1 | 1/1990 |
| EP | 0651968 A1 | 8/1990 |
| EP | 0 427 358 | 10/1990 |
| EP | 0 456 103 | 5/1991 |
| EP | 0581704 B1 | 7/1993 |
| EP | 0655138 B1 | 8/1993 |
| EP | 0894473 A2 | 1/1995 |
| EP | 0469966 | 8/1995 |
| EP | 0 908 146 | 10/1998 |
| EP | 0 930 046 | 10/1998 |
| EP | 1344187 | 9/2003 |
| EP | 1396233 | 3/2004 |
| EP | 1406203 | 4/2004 |
| EP | 1442715 A2 | 8/2004 |

| | | |
|---|---|---|
| EP | 1474782 | 11/2004 |
| EP | 1597701 | 11/2005 |
| EP | 1603076 | 12/2005 |
| EP | 1691687 | 8/2006 |
| EP | 1692633 | 8/2006 |
| EP | 1692657 | 8/2006 |
| EP | 1713015 | 10/2006 |
| FR | 2417970 | 2/1979 |
| FR | 2 618 211 | 7/1987 |
| GB | 2 094 590 | 2/1982 |
| GB | 2 164 856 | 10/1984 |
| JP | 61-94639 | 10/1984 |
| JP | 62-327 | 6/1985 |
| JP | 63-240851 | 3/1987 |
| JP | 3-267054 | 3/1990 |
| JP | 2765738 | 6/1998 |
| WO | WO 88/09151 | 12/1988 |
| WO | WO 89/05123 | 6/1989 |
| WO | WO 90/05494 | 5/1990 |
| WO | WO 91/03982 | 4/1991 |
| WO | WO 91/04711 | 4/1991 |
| WO | WO 91/07726 | 5/1991 |
| WO | WO 92/03090 | 3/1992 |
| WO | WO 92/06645 | 4/1992 |
| WO | WO 94/04938 | 3/1994 |
| WO | WO 94/23647 | 10/1994 |
| WO | WO 94/24933 | 11/1994 |
| WO | WO 95/07055 | 3/1995 |
| WO | WO 96/11624 | 4/1996 |
| WO | WO 96/32059 | 10/1996 |
| WO | WO 97/49453 | 6/1997 |
| WO | WO 97/36192 | 10/1997 |
| WO | WO 98/08554 | 3/1998 |
| WO | WO 98/38908 | 9/1998 |
| WO | WO 99/38449 | 1/1999 |
| WO | WO 99/15097 | 4/1999 |
| WO | WO 99/52094 | 4/1999 |
| WO | WO 99/21498 | 5/1999 |
| WO | WO 99/23956 | 5/1999 |
| WO | WO 99/26549 | 6/1999 |
| WO | WO 99/27839 | 6/1999 |
| WO | WO 99/29253 | 6/1999 |
| WO | WO 99/33406 | 7/1999 |
| WO | WO 99/37208 | 7/1999 |
| WO | WO 99/60939 | 12/1999 |
| WO | WO-0007652 | 2/2000 |
| WO | WO-0010034 | 2/2000 |
| WO | WO 01/30437 A1 | 5/2001 |
| WO | WO-0243003 | 5/2002 |
| WO | WO-02093292 | 11/2002 |
| WO | WO-02097735 | 12/2002 |
| WO | WO-02098292 | 12/2002 |
| WO | WO-03039600 A1 | 5/2003 |
| WO | WO-03060827 | 7/2003 |
| WO | WO-2004077359 | 9/2004 |
| WO | WO-2004096018 | 11/2004 |
| WO | WO-2005002444 | 1/2005 |
| WO | WO-2005048844 | 6/2005 |
| WO | WO-2005052838 | 6/2005 |
| WO | WO-2005057493 | 6/2005 |
| WO | WO-2005057498 | 6/2005 |
| WO | WO-2005084542 | 9/2005 |
| WO | WO-2005096227 | 10/2005 |
| WO | WO-2005111931 | 11/2005 |
| WO | WO-2006011850 | 2/2006 |
| WO | WO-2006017053 | 2/2006 |
| WO | WO-2006017392 | 2/2006 |
| WO | WO-2006028416 | 3/2006 |
| WO | WO-2006028474 | 3/2006 |
| WO | WO-2006069250 | 6/2006 |
| WO | WO-2006083236 | 8/2006 |
| WO | WO-2006088429 | 8/2006 |

OTHER PUBLICATIONS

Adams et al., Computer-Assisted Surgery, IEEE Computer Graphics & Applications, pp. 43-51, (May 1990).
Adams et al., "Orientation Aid for Head and Neck Surgeons," Innov. Tech. Biol. Med., vol. 13, No. 4, 1992, pp. 409-424.
Barrick et al., "Prophylactic Intramedullary Fixation of the Tibia for Stress Fracture in a Professional Athlete," Journal of Orthopaedic Trauma, vol. 6, No. 2, pp. 241-244 (1992).
Barrick et al., "Technical Difficulties with the Brooker-Wills Nail in Acute Fractures of the Femur," Journal of Orthopaedic Trauma, vol. 4, No. 2, pp. 144-150 (1990).
Barrick, "Distal Locking Screw Insertion Using a Cannulated Drill Bit: Technical Note," Journal of Orthopaedic Trauma, vol. 7, No. 3, 1993, pp. 248-251.
Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.
Benzel et al., "Magnetic Source Imaging: a Review of the Magnes System of Biomagnetic Technologies Incorporated," Neurosurgery, vol. 33, No. 2 (Aug. 1993), pp. 252-259.
Bergstrom et al. Stereotaxic Computed Tomography, Am. J. Roentgenol, vol. 127 pp. 167-170 (1976).
Bouazza-Marouf et al.; "Robotic-Assisted Internal Fixation of Femoral Fractures", IMECHE., pp. 51-58 (1995).
Brack et al., "Accurate X-ray Based Navigation in Computer-Assisted Orthopedic Surgery," CAR '98, pp. 716-722.
Brown, R., M.D., A Stereotactic Head Frame for Use with CT Body Scanners, Investigative Radiology © J.B. Lippincott Company, pp. 300-304 (Jul.-Aug. 1979).
Bryan, "Bryan Cervical Disc System Single Level Surgical Technique", Spinal Dynamics, 2002, pp. 1-33.
Bucholz et al., "Variables affecting the accuracy of stereotactic localizationusing computerized tomography," Journal of Neurosurgery, vol. 79, Nov. 1993, pp. 667-673.
Bucholz, R.D., et al. Image-guided surgical techniques for infections and trauma of the central nervous system, Neurosurg. Clinics of N.A., vol. 7, No. 2, pp. 187-200 (1996).
Bucholz, R.D., et al., A Comparison of Sonic Digitizers Versus Light Emitting Diode-Based Localization, Interactive Image-Guided Neurosurgery, Chapter 16, pp. 179-200 (1993).
Bucholz, R.D., et al., Intraoperative localization using a three dimensional optical digitizer, SPIE—The Intl. Soc. for Opt. Eng., vol. 1894, pp. 312-322 (Jan. 17-19, 1993).
Bucholz, R.D., et al., Intraoperative Ultrasonic Brain Shift Monitor and Analysis, Stealth Station Marketing Brochure (2 pages) (undated).
Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics and Computer-Assisted Surgery, Grenoble, France, pp. 459-466 (Mar. 19-22, 1997).
Champleboux et al., "Accurate Calibration of Cameras and Range Imaging Sensors: the NPBS Method," IEEE International Conference on Robotics and Automation, Nice, France, May 1992.
Champleboux, "Utilisation de Fonctions Splines pour la Mise au Point D'un Capteur Tridimensionnel sans Contact," Quelques Applications Medicales, Jul. 1991.
Cinquin et al., "Computer Assisted Medical Interventions," IEEE Engineering in Medicine and Biology, May/Jun. 1995, pp. 254-263.
Cinquin et al., "Computer Assisted Medical Interventions," International Advanced Robotics Programme, Sep. 1989, pp. 63-65.
Clarysse et al., "A Computer-Assisted System for 3-D Frameless Localization in Stereotaxic MRI," IEEE Transactions on Medical Imaging, vol. 10, No. 4, Dec. 1991, pp. 523-529.
Cutting M.D. et al., Optical Tracking of Bone Fragments During Craniofacial Surgery, Second Annual International Symposium on Medical Robotics and Computer Assisted Surgery, pp. 221-225, (Nov. 1995).
Feldmar et al., "3D-2D Projective Registration of Free-Form Curves and Surfaces," Rapport de recherche (Inria Sophia Antipolis), 1994, pp. 1-44.
Foley et al., "Fundamentals of Interactive Computer Graphics," The Systems Programming Series, Chapter 7, Jul. 1984, pp. 245-266.
Foley et al., "Image-guided Intraoperative Spinal Localization," Intraoperative Neuroprotection, Chapter 19, 1996, pp. 325-340.

Foley, "The StealthStation: Three-Dimensional Image-Interactive Guidance for the Spine Surgeon," Spinal Frontiers, Apr. 1996, pp. 7-9.
Friets, E.M., et al. A Frameless Stereotaxic Operating Microscope for Neurosurgery, IEEE Trans. on Biomed. Eng., vol. 36, No. 6, pp. 608-617 (Jul. 1989).
Gallen, C.C., et al., Intracranial Neurosurgery Guided by Functional Imaging, Surg. Neurol., vol. 42, pp. 523-530 (1994).
Galloway, R.L., et al., Interactive Image-Guided Neurosurgery, IEEE Trans. on Biomed. Eng., vol. 89, No. 12, pp. 1226-1231 (1992).
Galloway, R.L., Jr. et al, Optical localization for interactive, image-guided neurosurgery, SPIE, vol. 2164, pp. 137-145 (undated.
Germano, "Instrumentation, Technique and Technology", Neurosurgery, vol. 37, No. 2, Aug. 1995, pp. 348-350.
Gildenberg et al., "Calculation of Stereotactic Coordinates from the Computed Tomographic Scan," Neurosurgery, vol. 10, No. 5, May 1982, pp. 580-586.
Gomez, C.R., et al., Transcranial Doppler Ultrasound Following Closed Head Injury: Vasospasm or Vasoparalysis?, Surg. Neurol., vol. 35, pp. 30-35 (1991).
Gonzalez, "Digital Image Fundamentals," Digital Image Processing, Second Edition, 1987, pp. 52-54.
Gottesfeld Brown et al., "Registration of Planar Film Radiographs with Computer Tomography," Proceedings of MMBIA, Jun. '96, pp. 42-51.
Grimson, W.E.L., An Automatic Registration Method for Frameless Stereotaxy, Image Guided Surgery, and enhanced Reality Visualization, IEEE, pp. 430-436 (1994).
Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6, pp. 62-69 (Jun. 1999).
Gueziec et al., "Registration of Computed Tomography Data to a Surgical Robot Using Fluoroscopy: A Feasibility Study," Computer Science/Mathematics, Sep. 27, 1996, 6 pages.
Guthrie, B.L., Graphic-Interactive Cranial Surgery: The Operating Arm System, Handbook of Stereotaxy Using the CRW Apparatus, Chapter 13, pp. 193-211 (undated.
Hamadeh et al, "Kinematic Study of Lumbar Spine Using Functional Radiographies and 3D/2D Registration," TIMC UMR 5525—IMAG.
Hamadeh et al., "Automated 3-Dimensional Computed Tomographic and Fluorscopic Image Registration," Computer Aided Surgery (1998), 3:11-19.
Hamadeh et al., "Towards Automatic Registration Between CT and X-ray Images: Cooperation Between 3D/2D Registration and 2D Edge Detection," MRCAS '95, pp. 39-46.
Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).
Hatch, "Reference-Display System for the Integration of CT Scanning and the Operating Microscope," Thesis, Thayer School of Engineering, Oct. 1984, pp. 1-189.
Hatch, et al., "Reference-Display System for the Integration of CT Scanning and the Operating Microscope", Proceedings of the Eleventh Annual Northeast Bioengineering Conference, Mar. 14-15, 1985, pp. 252-254.
Heilbrun et al., "Preliminary experience with Brown-Roberts-Wells (BRW) computerized tomography stereotaxic guidance system," Journal of Neurosurgery, vol. 59, Aug. 1983, pp. 217-222.
Heilbrun, M.D., Progressive Technology Applications, Neurosurgery for the Third Millenium, Chapter 15, J. Whitaker & Sons, Ltd., Amer. Assoc. of Neurol. Surgeons, pp. 191-198 (1992).
Heilbrun, M.P., Computed Tomography—Guided Stereotactic Systems, Clinical Neurosurgery, Chapter 31, pp. 564-581 (1983).
Heilbrun, M.P., et al., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).
Henderson et al., "An Accurate and Ergonomic Method of Registration for Image-guided Neurosurgery," Computerized Medical Imaging and Graphics, vol. 18, No. 4, Jul.-Aug. 1994, pp. 273-277.
Hoerenz, "The Operating Microscope I. Optical Principles, Illumination Systems, and Support Systems," Journal of Microsurgery, vol. 1, 1980, pp. 364-369.
Hofstetter et al., "Fluoroscopy Based Surgical Navigation—Concept and Clinical Applications," Computer Assisted Radiology and Surgery, 1997, pp. 956-960.
Homer et al., "A Comparison of CT-Stereotaxic Brain Biopsy Techniques," Investigative Radiology, Sep.-Oct. 1984, pp. 367-373.
Hounsfield, "Computerized transverse axial scanning (tomography): Part 1. Description of system," British Journal of Radiology, vol. 46, No. 552, Dec. 1973, pp. 1016-1022.
Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.
Jacques et al., "Computerized three-dimensional stereotaxic removal of small central nervous system lesion in patients," J. Neurosurg., vol. 53, Dec. 1980, pp. 816-820.
Joskowicz et al., "Computer-Aided Image-Guided Bone Fracture Surgery: Concept and Implementation," CAR '98, pp. 710-715.
Kall, B., The Impact of Computer and Imgaging Technology on Stereotactic Surgery, Proceedings of the Meeting of the American Society for Stereotaclic and Functional Neurosurgery, pp. 10-22 (1987).
Kato, A., et al., A frameless, armless navigational system for computer-assisted neurosurgery, J. Neurosurg., vol. 74, pp. 845-849 (May 1991).
Kelly et al., "Computer-assisted stereotaxic laser resection of intra-axial brain neoplasms," Journal of Neurosurgery, vol. 64, Mar. 1986, pp. 427-439.
Kelly et al., "Precision Resection of Intra-Axial CNS Lesions by CT-Based Stereotactic Craniotomy and Computer Monitored CO2 Laser," Acta Neurochirurgica, vol. 68, 1983, pp. 1-9.
Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).
Kelly, P.J., Computer-Directed Stereotactic Resection of Brain Tumors, Neurologica Operative Atlas, vol. 1, No. 4, pp. 299-313 (1991).
Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).
Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).
Kim, W.S. et al., A Helmet Mounted Display for Telerobotics, IEEE, pp. 543-547 (1988).
Klimek, L., et al., Long-Term Experience with Different Types of Localization Systems in Skull-Base Surgery, Ear, Nose & Throat Surgery, Chapter 51, pp. 635-638 (undated).
Kosugi, Y., et al., An Articulated Neurosurgical Navigation System Using MRI and CT Images, IEEE Trans. on Biomed, Eng. vol. 35, No. 2, pp. 147-152 (Feb. 1988).
Krybus, W., et al., Navigation Support for Surgery by Means of Optical Position Detection, Computer Assisted Radiology Proceed. of the Intl. Symp. CAR '91 Computed Assisted Radiology, pp. 362-366 (Jul. 3-6, 1991).
Kwoh, Y.S., Ph.D., et al., A New Computerized Tomographic-Aided Robotic Stereotaxis System, Robotics Age, vol. 7, No. 6, pp. 17-22 (Jun. 1985).
Laitinen et al., "An Adapter for Computed Tomography-Guided, Stereotaxis," Surg. Neurol., 1985, pp. 559-566.
Laitinen, "Noninvasive multipurpose stereoadapter," Neurological Research, Jun. 1987, pp. 137-141.
Lavallee et al, "Matching 3-D Smooth Surfaces with their 2-D Projections using 3-D Distance Maps," SPIE, vol. 1570, Geometric Methods in Computer Vision, 1991, pp. 322-336.
Lavallee et al., "Computer Assisted Driving of a Needle into the Brain," Proceedings of the International Symposium CAR '89, Computer Assisted Radiology, 1989, pp. 416-420.

Lavallee et al., "Computer Assisted Interventionist Imaging: The Instance of Stereotactic Brain Surgery," North-Holland MEDINFO 89, Part 1, 1989, pp. 613-617.
Lavallee et al., "Computer Assisted Spine Surgery: A Technique for Accurate Transpedicular Screw Fixation Using CT Data and a 3-D Optical Localizer," TIMC, Faculte de Medecine de Grenoble.
Lavallee et al., "Image guided operating robot: a clinical application in stereotactic neurosurgery," Proceedings of the 1992 IEEE International Conference on Robotics and Automation, May 1992, pp. 618-624.
Lavallee et al., "Matching of Medical Images for Computed and Robot Assisted Surgery," IEEE EMBS, Orlando, 1991.
Lavallee, "A New System for Computer Assisted Neurosurgery," IEEE Engineering in Medicine & Biology Society 11th Annual International Conference, 1989, pp. 0926-0927.
Lavallee, "Vl Adaption de la Methodologie a Quelques Applications Cliniques," Chapitre VI, pp. 133-148.
Lavallee, S., et al., Computer Assisted Knee Anterior Cruciate Ligament Reconstruction First Clinical Tests, Proceedings of the First International Symposium on Medical Robotics and Computer Assisted Surgery, pp. 11-16 (Sep. 1994).
Lavallee, S., et al., Computer Assisted Medical Interventions, NATO ASI Series, vol. F 60, 3d Imaging in Medic., pp. 301-312 (1990).
Leavitt, D.D., et al., Dynamic Field Shaping to Optimize Stereotactic Radiosurgery, I.J. Rad. Onc. Biol. Physc., vol. 21, pp. 1247-1255 (1991).
Leksell et al., "Stereotaxis and Tomography—A Technical Note," ACTA Neurochirurgica, vol. 52, 1980, pp. 1-7.
Lemieux et al., "A Patient-to-Computed-Tomography Image Registration Method Based on Digitally Reconstructed Radiographs," Med. Phys. 21 (11), Nov. 1994, pp. 1749-1760.
Levin et al., "The Brain: Integrated Three-dimensional Display of MR and PET Images," Radiology, vol. 172, No. 3, Sep. 1989, pp. 783-789.
Maurer, Jr., et al., Registration of Head CT Images to Physical Space Using a Weighted Combination of Points and Surfaces, IEEE Trans. on Med. Imaging, vol. 17, No. 5, pp. 753-761 (Oct. 1998).
Mazier et al., "Computer-Assisted Interventionist Imaging: Application to the Vertebral column Surgery," Annual International Conference of the IEEE Engineering in Medicine and Biology Society, vol. 12, No. 1, 1990, pp. 0430-0431.
Mazier et al., Chirurgie de la Colonne Vertebrale Assistee par Ordinateur: Appication au Vissage Pediculaire, Innov. Tech. Biol. Med., vol. 11, No. 5, 1990, pp. 559-566.
McGirr, S., M.D., et al., Stereotactic Resection of Juvenile Pilocytic Astrocytomas of the Thalamus and Basal Ganglia, Neurosurgery, vol. 20, No. 3, pp. 447-452, (1987).
Merloz, et al., "Computer Assisted Spine Surgery", Clinical Assisted Spine Surgery, No. 337, pp. 86-96.
Ng, W.S. et al., Robotic Surgery—A First-Hand Experience in Transurethral Resection of the Prostate Surgery, IEEE Eng. In Med. and Biology, pp. 120-125 (Mar. 1993).
Pelizzari et al., "Accurate Three-Dimensional Registration of CT, PET, and/or MR Images of the Brain," Journal of Computer Assisted Tomography, Jan./Feb. 1989, pp. 20-26.
Pelizzari et al., "Interactive 3D Patient-Image Registration," Information Processing in Medical Imaging, 12th International Conference, IPMI '91, Jul. 7-12, 136-141 (A.C.F. Colchester et al. eds. 1991).
Pelizzari et al., No. 528—"Three Dimensional Correlation of PET, CT and MRI Images," The Journal of Nuclear Medicine, vol. 28, No. 4, Apr. 1987, p. 682.
Penn, R.D., et al., Stereotactic Surgery with Image Processing of Computerized Tomographic Scans, Neurosurgery, vol. 3, No. 2, pp. 157-163 (Sep.-Oct. 1978).
Phillips et al., "Image Guided Orthopaedic Surgery Design and Analysis," Trans Inst. MC, vol. 17, No. 5, 1995, pp. 251-264.
Pixsys, 3-D Digitizing Accessories, by Pixsys (marketing brochure)(undated) (2 pages).
Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.
Prestige Cervical Disc System Surgical Technique, 12 pgs.
Reinhardt et al., "CT-Guided 'Real Time' Stereotaxy," ACTA Neurochirurgica, 1989.
Reinhardt, H., et al., A Computer-Assisted Device for Intraoperative CT-Correlated Localization of Brain Tumors, pp. 51-58 (1988).
Reinhardt, H.F. et al., Sonic Stereometry in Microsurgical Procedures for Deep-Seated Brain Tumors and Vascular Malformations, Neurosurgery, vol. 32, No. 1, pp. 51-57 (Jan. 1993).
Reinhardt, H.F., et al., Mikrochirugische Entfernung tiefliegender Gefäßmißbildungen mit Hilfe der Sonar-Stereometrie (Microsurgical Removal of Deep-Seated Vascular Malformations Using Sonar Stereometry). Ultraschall in Med. 12, pp. 80-83 (1991).
Reinhardt, Hans. F., Neuronavigation: A Ten-Year Review, Neurosurgery, pp. 329-341 (undated).
Roberts et al., "A frameless stereotaxic integration of computerized tomographic imaging and the operating microscope," J. Neurosurg., vol. 65, Oct. 1986, pp. 545-549.
Rosenbaum et al., "Computerized Tomography Guided Stereotaxis: A New Approach," Applied Neurophysiology, vol. 43, No. 3-5, 1980, pp. 172-173.
Sautot, "Vissage Pediculaire Assiste Par Ordinateur," Sep. 20, 1994.
Schueler et al., "Correction of Image Intensifier Distortion for Three-Dimensional X-Ray Angiography," SPIE Medical Imaging 1995, vol. 2432, pp. 272-279.
Selvik et al., "A Roentgen Stereophotogrammetric System," Acta Radiologica Diagnosis, 1983, pp. 343-352.
Shelden et al., "Development of a computerized microsteroetaxic method for localization and removal of minute CNS lesions under direct 3-D vision," J. Neurosurg., vol. 52, 1980, pp. 21-27.
Simon, D.A., Accuracy Validation in Image-Guided Orthopaedic Surgery, Second Annual Intl. Symp. on Med. Rob. an Comp-Assisted surgery, MRCAS '95, pp. 185-192 (undated).
Smith et al., "Computer Methods for Improved Diagnostic Image Display Applied to Stereotactic Neurosurgery," Automedical, vol. 14, 1992, pp. 371-382 (4 unnumbered pages).
Smith et al., "The Neurostation™—A Highly Accurate, Minimally Invasive Solution to Frameless Stereotactic Neurosurgery," Computerized Medical Imaging and Graphics, vol. 18, Jul.-Aug. 1994, pp. 247-256.
Smith, K.R., et al. Multimodality Image Analysis and Display Methods for Improved Tumor Localization in Stereotactic Neurosurgery, Annul Intl. Conf. of the IEEE Eng. in Med. and Biol. Soc., vol. 13, No. 1, p. 210 (1991).
Tan, K., Ph.D., et al., A frameless stereotactic approach to neurosurgical planning based on retrospective patient-image registration, J Neurosurgy, vol. 79, pp. 296-303 (Aug. 1993).
The Laitinen Stereotactic System, E2-E6.
Thompson, et al., A System for Anatomical and Functional Mapping of the Human Thalamus, Computers and Biomedical Research, vol. 10, pp. 9-24 (1977).
Trobaugh, J.W., et al., Frameless Stereotactic Ultrasonography: Method and Applications, Computerized Medical Imaging and Graphics, vol. 18, No. 4, pp. 235-246 (1994).
Viant et al., "A Computer Assisted Orthopaedic System for Distal Locking of Intramedullary Nails," Proc. of MediMEC '95, Bristol, 1995, pp. 86-91.
Von Hanwhr et al., Foreword, Computerized Medical Imaging and Graphics, vol. 18, No. 4, pp. 225-228, (Jul.-Aug. 1994).
Wang, M.Y., et al., An Automatic Technique for Finding and Localizing Externally Attached Markers in CT and MR volume Images of the Head, IEEE Trans. on Biomed. Eng., vol. 43, No. 6, pp. 627-637 (Jun. 1996).
Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.
Watanabe, "Neuronavigator," Igaku-no-Ayumi, vol. 137, No. 6, May 10, 1986, pp. 1-4.
Watanabe, E., M.D., et al., Open Surgery Assisted by the Neuronavigator, a Stereotactic, Articulated, Sensitive Arm, Neurosurgery, vol. 28, No. 6, pp. 792-800 (1991).
Weese et al., "An Approach to 2D/3D Registration of a Vertebra in 2D X-ray Fluoroscopies with 3D CT Images," pp. 119-128.

"Advanced Drug Delivery: Technologies, Applications & Markets Jul. 2003, A Kalorama Information Market Intelligence Report." (Jul. 2003) Kalorama Information 432 sheets.

"Interventional Radiology Grand Rounds. Topic: Central Venous Access." Society of Interventional Radiology, (2004) 4 sheets.

Arndt, "Neopharm Investigators Present Final Results of Peritumoral vs. Intratumoral Infusion of IL13-PE38QQR from Phase1 Clinical Studies at the American Society of Clinical Oncology Meeting." NeoPharm. Biowire2k 4st Annual Meeting of the American Society of Clinical Oncology. Business Wire (May 17, 2005) www.businesswire.com/news/home/20050517005098/en/NeoPharm-Investigators-Pr accessed Jul. 27, 2011.

Beghetto, M.G., et al. Parenteral Nutrition as a Risk Factor for Central Venous Catheter-Related Infection. Journal of Parenteral and Enteral Nutrition 29(5): (Sep. 4, 2005) pp. 367-373. http://www.redorbit.com/news/health/229618/parenteral_nutrition_as_a_risk_factor_for_central_venous_catheter/ (accessed Jul. 27, 2011).

Finnis, Kirk W., et al., "Three-Dimensional Database of Subcortical Electrophysiology for Image-Guided Stereotactic Functional Neurosurgery," IEEE Transactions of Medical Imaging, vol. 22, No. 1 (Jan. 2003) pp. 93-104.

Flanigan, M. et al.. Peritoneal Catheters and Exit-Site Practices Toward Optimum Peritoneal Access: A Review of Current Developments. Peritoneal Dialysis International. (2005) vol. 25, pp. 132-139.

Fletcher, S.J., et al. "Editorial II. Safe placement of central venous catheters: where should the tip of the catheter lie?" Oxford Journals, British Journal of Anaesthesia (2000) vol. 85 Issue 2, August. pp. 188-191.

Hanas, M.D., Ragnar. "Indwelling_Catheters_for_Injections. How to Reduce Injection Anxiety. Insuflon." (Jun. 2003) Children with Diabetes. http://www.childrenwithdiabetes.com/d_06_311.htm web accessed Jul. 27, 2011.

Hayashi, Y., et al. "Optimal Placement of CVP Catheter in Paediatric Cardiac Patients." Canadian Journal of Anesthesia, (1995) 42:6 pp. 479-482.

Hodge, D. et al. "Diagnosis, prevention, and management of catheter related bloodstream infection during long term parenteral nutrition." Arch. Dis. Child. Fetal Neonatal Ed. (2002) vol. 87 pp. F21-F24.

Hoenecke, Heinz, R., et al. "Continuous Local Anesthetic Infiltration," Case Report. Orthopedic Technology Review (Mar./Apr. 2002) vol. 3 No. 2. http://www.orthopedictechreview.com/issues/marapr02/case.htm. Said url is no longer valid. The article can be found using the Wayback Machine archive at: http://web.archive.org/web/20060315052636/http://www.orthopedictechreview.com/issues/marapr02/case.htm. Accessed and printed Aug. 11, 2011.

Kunwar, S., et al. "Peritumoral convection-enhanced delivery (CED) of IL13-PE38QQR (IL13PE): Results of multicenter phase 1 studies in recurrent High Grade Glioma (HGG)." Abstracts from the World Federation of Neuro-Oncology Second Quadrennial Meeting and Sixth Meeting of the European Association for Neuro-Oncology, Edinburgh, UK. (May 5-8, 2005) p. 311 Society for Neuro-Oncology.

Müller, M., et al. "Issues in Pharmacokinetics and Pharmacodynamics of Anti-Infective Agents: Distribution in Tissue." Antimicrobial Agents and Chemotherapy, MINIREVIEW (2004) vol. 48, No. 5. pp. 1441-1453.

Renard, E., et. al. "Catheter Complications Associated with Implantable Systems for Peritoneal Insulin Delivery. An Analysis of Frequency, Predisposing Factors, and Obstructing Materials." Diabetes Care (Mar. 1995) vol. 18, No. 3. pp. 300-306.

Vande Walle, et al. "Use of Bicarbonate/Lactate Buffered Dialysate with Nighttime Cycler, Associated with a Daytime Dwell with Icodextrin, May Result in Alkalosis in Children." Advances in Peritoneal Dialysis (2004) vol. 20, pp. 222-225.

Vesely, T.M., "Central Venous Catheter Tip Position: A Continuing Controversy." J Vasc Intery Radiol (2003) vol. 14, No. 5. pp. 527-534.

Washburn, Kimberly, K, et al. "Surgical Technique for Peritoneal Dialysis Catheter Placement in the Pediatric Patient: A North American Survey." Advances in Peritoneal Dialysis (2004) vol. 20, pp. 218-221.

Zürcher, Matthias et al. "Colonization and Bloodstream Infection with Single-Versus Multi-Lumen Central Venous Catheters: A Quantitative Systematic Review." Anesthesia & Analgesia (2004) vol. 99, pp. 177-182.

International Preliminary Report on Patentability for PCT/US2007/009931 mailed Jan. 20, 2009, claiming priority to U.S. Appl. No. 11/683,796, filed Mar. 8, 2007.

International Search Report and Written Opinion for PCT/US2007/009931 mailed Nov. 14, 2007, claiming priority to U.S. Appl. No. 11/683,796, filed Mar. 8, 2007.

iPlan® Stereotaxy Software, BrainLab, http://www.brainlab.com/scripts/website_english.asp?menuDeactivate=1&articleID=1842&articleTypeID=27&pageTypeID=4&article_short_headline=iPlan%AE%20Stereotaxy printed Apr. 1, 2009.

Merloz, et al., "Computer Assisted Spine Surgery", Clinical Assisted Spine Surgery, No. 337 (1997) pp. 86-96.

NeuroSight™ Cranial Module, Radionics™, Jul. 27, 2003 http://www.radionics.com/products/frameless/omnisight/omnisight_modules.shtml#neuro accessed and printed on Apr. 1, 2009 through the Wayback Machine at http://www.archive.org/web/web.php.

VectorVision® cranial Navigation Software, BrainLab, http://www.brainlab.com/scripts/website_english.asp?menuDeactivate=1&articleID=593&articleTypeID=27&pageTypeID=4&article_short_headline=VectorVision%AE%20%20cranial printed Apr. 1, 2009.

Versweyveld, Leslie, "Scientists in Singapore develop Virtual Brain Bench for stereotactic frame neurosurgery," VMW Virtual Medical Worlds Monthly, printed Apr. 1, 2009 (3 pages).

Wood et al. Technologies for Guidance of Radiofrequency Ablation in the Multimodality Interventional Suite of the Future. J Vasc Intery Radiol. Jan. 2007; 18(1 Pt 1): 9-24. doi:1 0.1 016/j.jvir.2006.1 0.013.

Butz et al. Pre- and Intra-operative Planning and Simulation of Percutaneous Tumor Ablation, Proceedings of The Third International Conference on Medical Image Computing and Computer-Assisted Intervention, p. 317-326, Oct. 11-14, 2000.

International Search Report and Written Opinion for PCT/US2007/009820 mailed Sep. 21, 2007 claiming benefit of the current case.

International Preliminary Report on Patentability for PCT/US2007/009820 mailed Oct. 30, 2008 claiming benefit of U.S. Appl. No. 11/409,499.

* cited by examiner

METHOD AND APPARATUS FOR OPTIMIZING A THERAPY

FIELD

The present disclosure relates generally to providing a therapy to a patient, and more specifically, to a method and apparatus for optimizing a therapy for a patient based upon patient specific information.

BACKGROUND

Typically a standard or general drug delivery protocol/methodology can be used for most patients. Examples include generally known or existing catheterization and miscellaneous protocols. These protocols rarely contain criteria that are patient-specific (e.g., specific target positions or other locational constraints within the context of a particular patient's anatomy or medical history). Many protocols use generic anatomical landmark references for catheter placement or positioning.

Drug delivery technology has made advancements in fighting diseases that in the past were viewed as untreatable, such as metabolic diseases, cancer, hormonal disorders, and viral infections. The compounds used to treat such diseases are typically molecularly large and can be unstable, requiring injection or intravenous infusion. Challenges in drug delivery effectiveness include drug insolubility (e.g., in water), non-specificity/cytotoxicity of drugs, other drug side effects, deactivation by body system enzymes, low bioavailability and/or variability in bioavailability. Significantly, the appropriate targeting of drug therapy to systems (e.g., tissue) is a significant factor in these drug effectiveness considerations.

The effectiveness of most drugs depends on reaching target tissues, not plasma, and is impacted by inequilibrium between blood and tissue. Targeting issues affect both local and regional drug delivery strategies, effecting intra-arterial, intrathecal chemotherapy and intra-articular injections. Also, impaired drug penetration and blood-tissue inequilibrium can cause failures of the drug therapy or other complications. The therapy targeting patent landscape focuses more on modifications to pill coatings, engineering of therapies to target cellular receptors, and drug diffusion detection using MRI sensors.

While various navigation systems are known to allow for certain procedures, such as navigating an instrument relative to a patient or navigating an implant relative to a patient the navigation systems are generally used to determine a position of an instrument or implant relative to a selected portion of a patient or anatomy. It may be desirable, however, to track or know a location of a delivery device relative to a portion of a patient for achieving various delivery protocols. Various protocols are known or can be developed for applying or positioning a selected material, such as a medication, an antiseptic, an anesthesia, or other appropriate materials relative to a selected area. For example, treatment for a particular malady, such as a cancerous tumor, can include positioning a biological compound or a bioactive compound relative to the tumor. Nevertheless, the positioning of the chemical relative to the affected area can be difficult depending on the position of the affected area and path necessary to reach the affected area. Therefore, it is desirable to provide a system that allows for optimizing a therapy that can include the precise positioning of a delivery device and bioactive material relative to a selected area of a patient.

SUMMARY

A material can be positioned or delivered to a patient with a selected protocol. A navigation system can assist in determining a position of a delivery device relative to a portion of the patient. Further, an automated system can assist in providing a selected or optimal pathway or optimal position of a delivery device based upon the protocol and specific patient data. For example, a system can determine an optimal entry point, pathway, and final position of a catheter to deliver a selected bioactive component to a selected area in a patient. The pathway, entry point, and final destination can be based upon patient specific data and selected protocol.

Medical imagery can be a source of patient data. It can be integrated with a variety of other drug and patient-specific information and user inputs, to develop an optimal method and path for drug delivery or other therapies. It can allow visualization of optimal delivery conditions and constraints and can provide a base map for exploring drug delivery trajectories from entry to target, providing the ability to also determine e.g., appropriate catheter type for therapy implementation.

A range of imaging techniques are known to be useful in drug distribution studies, such as planar gamma scintigraphy (PGS), single photon emission computed tomography (SPECT), positron emission tomography (PET) and magnetic resonance spectroscopy. Overall, these methods are valuable for their ability to assist in determining a path of a drug from the plasma to anatomically defined regions.

According to various embodiments a method of providing an optimized therapy to a patient is disclosed. The method can include selecting a therapy protocol and providing information relating to the patient. A processor can execute a program to determine an optimized plan to optimize the therapy protocol in the patient based on the provided information related to the patient.

According to various embodiments a system to determine an optimized therapy for a patient is disclosed. The system can include a first input system to input image data of the patient, a second input system to input information regarding the patient, and a third input system to input general therapy protocol. A processor can perform instructions to form a proposed plan. The instructions can include determining a selected location in the image data, determining an entry point to the patient, or determining a path to reach the selected location from the entry point.

According to various embodiments a method of automatically determining an optimized therapy for a patient based upon general therapy protocols and patient specific information is disclosed. The method can include providing a general therapy protocol and providing image data of the patient. A processor can determine a plan based upon the provided general therapy protocol and the provided image data to determine an optimal plan of therapy for the patient. An instrument can be moved based upon the determined plan.

BRIEF DESCRIPTION OF THE DRAWINGS

The present teachings will become more fully understood from the detailed description and the accompanying drawings, wherein.

DETAILED DESCRIPTION OF VARIOUS EMBODIMENTS

The following description of various embodiments is merely exemplary in nature and is in no way intended to limit the teachings, its application, or uses. Further, it will be understood that while various protocols and patient specific data are discussed herein, the specific protocols and patient data are merely exemplary and provided for ease of the discussion of the present disclosure. Therefore, although various specific examples may be provided, it will be understood that the method and apparatus for optimizing a therapy as described herein can be applied to any appropriate patient, disease, injury, or protocol.

Figure 1:
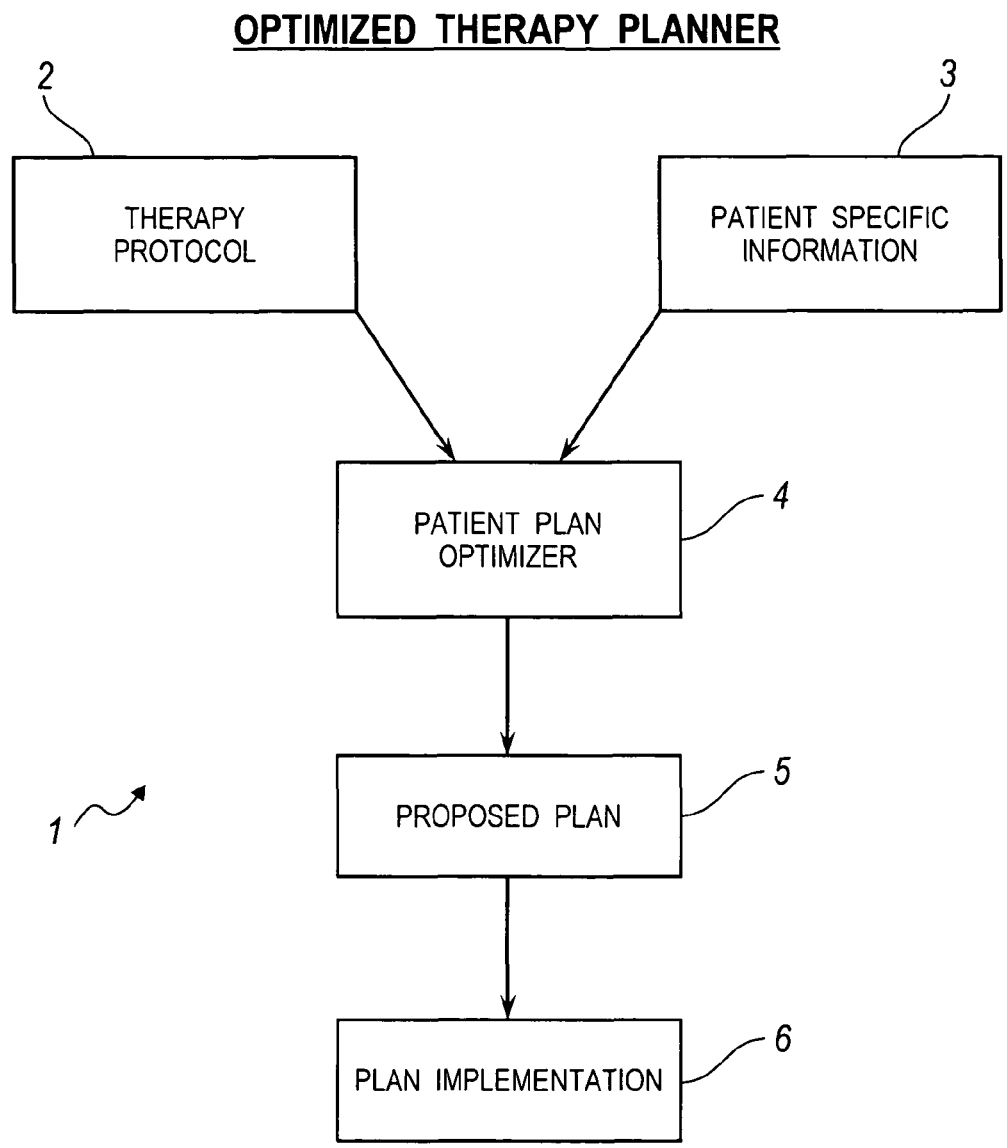
FIG. 1 is an overview flow chart of a process to optimize a therapy.

FIG. 1 generally illustrates a broad overview flowchart of an optimized therapy planner 1. The optimized therapy planner 1 can include the input of a therapy protocol in block 2 and patient specific information in block 3 into a patient plan optimizer in block 4. The therapy protocol can include any appropriate protocol such as generally known protocols or developed protocols for various therapies or drug deliveries. For example, a protocol may include a desired or selected location of a delivery device relative to the malady (e.g. a brain tumor) drug delivery rates, a period of drug delivery, or other appropriate protocol information, including pharmokinetics. The Therapy Protocol may also include information regarding various devices, delivery methods, surgical systems, etc.

Patient specific information acquired or inputted in block 3 can include image data of a patient, prior history of a patient (e.g., prior procedures, drug allergies, age, and gender). Therefore, the patient specific information can be any appropriate information that can be specific to a patient to be used by the patient plan optimizer in block 4.

The patient plan optimizer in block 4 can include a system that can determine an optimized therapy or optimal plan for the therapy for the specific patient based upon the patient specific information and the general therapy protocol. The patient plan optimizer in block 4 can use various search techniques based upon the patient specific information to form candidate plans. The patient plan optimizer in block 4 can also then rate the goodness of the plans to provide each of the candidate plans with a plan goodness value (PGV).

The patient plan optimizer in block 4 can propose a single plan in proposed plan block 5 or propose numerous plans. The patient plan optimizer in block 4 can provide only the candidate plan with the highest plan goodness value as the proposed plan in block 5 or the patient plan optimizer in block 4 can provide a plurality of candidate plans with its associated plan goodness value as a proposed plan in block 5. Therefore, a user can either choose the plan to be used, also referred to as the optimal plan, or the patient plan optimizer in block 4 can provide only the optimal plan in proposed plan block 5.

Finally, the optimized plan can be implemented in block 6. Plan implementation in block 6 can include any appropriate method such as manual methods, navigated methods, or combinations thereof. For example, the proposed plan in block 5 can include a final location and a path for an instrument (an EG or catheter) to follow and a navigation implementation can be used to track the catheter relative to the image data that can be patient specific information in block 3 to track and ensure the completion of the proposed plan from block 5.

It will be understood that various protocols can be used in the therapy protocol block 2, including those discussed herein. Further, the patient specific information can include any appropriate patient specific information, such as image data of the patient to assist in determining various anatomical features (e.g., anatomical surfaces) which can assist in forming the proposed plan in block 5. Further, the patient plan optimizer in block 4 can be an algorithm that is executable by a processor, such as a microprocessor, to determine the proposed plan in block 5.

Figure 2:
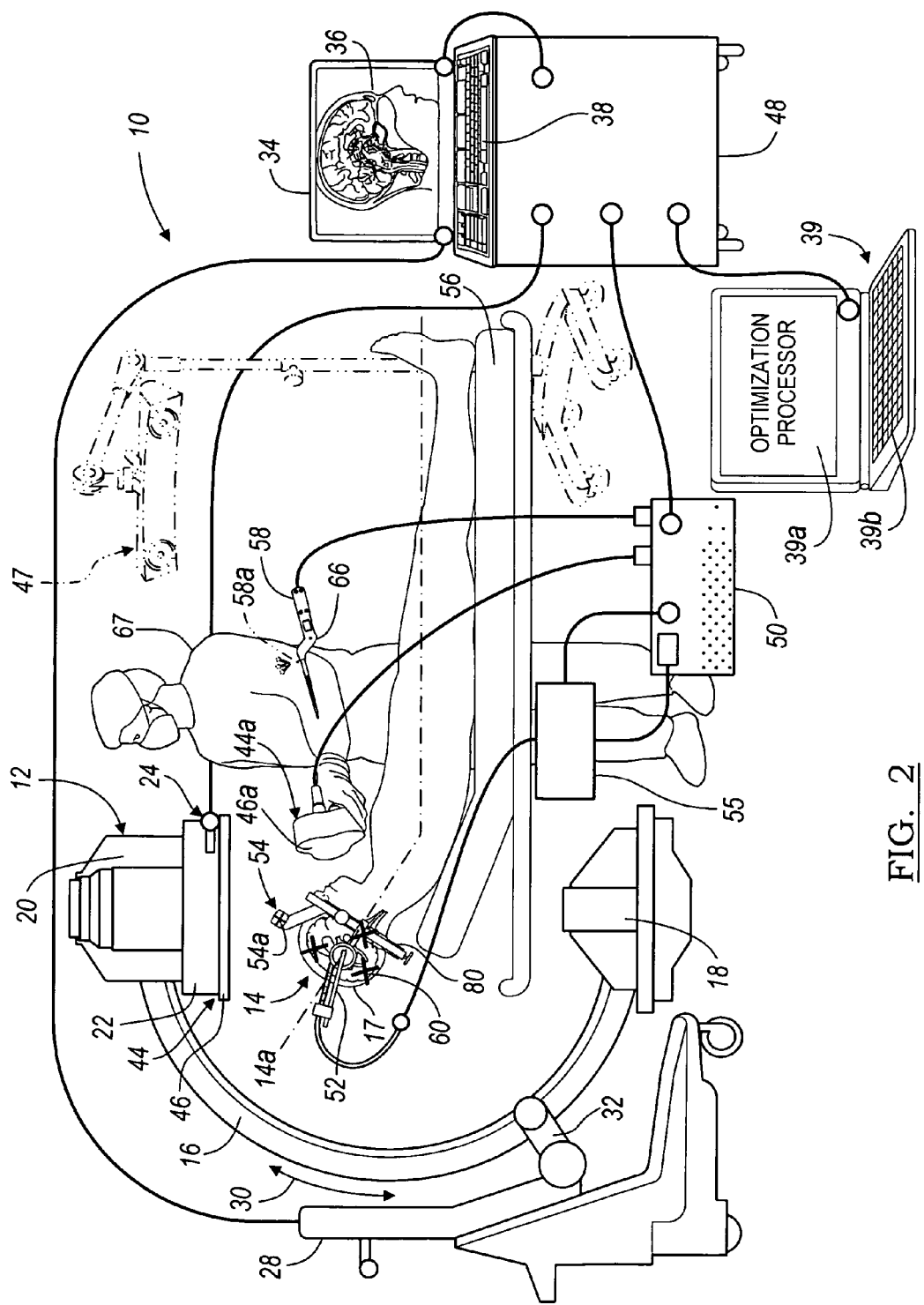
FIG. 2 is a diagram of a navigation system according to various teachings.

FIG. 2 is a diagram illustrating an overview of an image-guided navigation system 10 that can be used for various procedures in relation to the optimized therapy plan. The navigation system 10 can be used to track the location of a device, such as a delivery device, relative to a patient 14 to assist in the implementation of the plan in block 5, and discussed herein. It should further be noted that the navigation system 10 may be used to navigate or track other devices including: catheters, probes, needles, etc. Moreover, the navigated device may be used in any region of the body. The navigation system 10 and the various devices may be used in any appropriate procedure, such as one that is generally minimally invasive, arthroscopic, percutaneous, stereotactic, or an open procedure. Although an exemplary navigation system 10 including an imaging system 12 are discussed herein, one skilled in the art will understand that the disclosure is merely for clarity of the present discussion and any appropriate imaging system, navigation system, patieitn specific data, and non-patient specific data can be used.

The navigation system 10 can include an optional imaging device 12 that is used to acquire pre-, intra-, or post-operative or real-time image data of a patient 14. The image data acquired with the imaging device 12 can be used as part of the patient specific information in block 3. Alternatively various imageless systems can be used or images from atlas models can be used to produce patient images, such as those disclosed in U.S. patent application Ser. No. 10/687,539, filed Oct. 16, 2003, entitled "METHOD AND APPARATUS FOR SURGICAL NAVIGATION OF A MULTIPLE PIECE CONSTRUCT FOR IMPLANTATION", incorporated herein by reference. The optional imaging device 12 is, for example, a fluoroscopic x-ray imaging device that may be configured as a C-arm 16 having an x-ray source 18, an x-ray receiving section 20, an optional calibration and tracking target 22 and optional radiation sensors 24. Image data may also be acquired using other imaging devices, such as those discussed above and herein.

The calibration and tracking target 22 includes calibration markers 26 (see FIGS. 3A-3B), further discussed herein. An optional imaging device controller 28 that may control the imaging device 12, such as the C-arm 16, can capture the x-ray images received at the receiving section 20 and store the images for later use. The controller 28 may also be separate from the C-arm 16 and/or control the rotation of the C-arm 16. For example, the C-arm 16 can move in the direction of arrow 30 or rotate about a longitudinal axis 14*a* of the patient 14, allowing anterior or lateral views of the patient 14 to be imaged. Each of these movements involves rotation about a mechanical axis 32 of the C-arm 16.

In the example of FIG. 2, the longitudinal axis 14*a* of the patient 14 is substantially in line with the mechanical axis 32 of the C-arm 16. This enables the C-arm 16 to be rotated relative to the patient 14, allowing images of the patient 14 to be taken from multiple directions or about multiple planes. An example of a fluoroscopic C-arm x-ray device that may be used as the optional imaging device 12 is the "Series 9600 Mobile Digital Imaging System," from OEC Medical Systems, Inc., of Salt Lake City, Utah. Other exemplary fluoroscopes include bi-plane fluoroscopic systems, ceiling fluoroscopic systems, cath-lab fluoroscopic systems, fixed C-arm fluoroscopic systems, isocentric C-arm fluoroscopic systems, 3D fluoroscopic systems, etc.

In operation, the C-arm 16 generates x-rays from the x-ray source 18 that propagate through the patient 14 and calibration and/or tracking target 22, into the x-ray receiving section 20. It will be understood that the tracking target need not include a calibration portion. The receiving section 20 generates image data representing the intensities of the received x-rays. Typically, the receiving section 20 includes an image intensifier that first converts the x-rays to visible light and a charge coupled device (CCD) video camera that converts the visible light into digital image data. Receiving section 20 may also be a digital device that converts x-rays directly to digital image data for forming images, thus potentially avoiding distortion introduced by first converting to visible light. With this type of digital C-arm, which is generally a flat panel device, the optional calibration and/or tracking target 22 and the calibration process discussed below may be eliminated. Also, the calibration process may be eliminated or not used at all for various procedures. Alternatively, the imaging device 12 may only take a single image with the calibration and tracking target 22 in place. Thereafter, the calibration and tracking target 22 may be removed from the line-of-sight of the imaging device 12.

Two dimensional fluoroscopic images that may be taken by the imaging device 12 are captured and stored in the C-arm controller 28. Multiple two-dimensional images taken by the imaging device 12 may also be captured and assembled to provide a larger view or image of a whole region of a patient, as opposed to being directed to only a portion of a region of the patient. For example, multiple image data of a patient's leg may be appended together to provide a full view or complete set of image data of the leg that can be later used to follow contrast agent, such as Bolus tracking.

The image data can then be forwarded from the C-arm controller 28 to a navigation computer and/or processor controller or work station 34 having a display 36 and a user interface 38. The work station 34 can include an optimization processor, as discussed herein, or a separate optimization processor 39 can be included. The optimization processor can also include a display 39a and a user input 39b. It will also be understood that the image data is not necessarily first retained in the controller 28, but may also be directly transmitted to the navigation computer 34.

The work station 34 or optimization processor 39 provides facilities for displaying the image data as an image on the display 36, saving, digitally manipulating, or printing a hard copy image of the of the received image data. The user interface 38, which may be a keyboard, mouse, touch pen, touch screen or other suitable device, allows a physician or user to provide inputs to control the imaging device 12, via the C-arm controller 28, or adjust the display settings of the display 36. The work station 34 may also direct the C-arm controller 28 to adjust the rotational axis 32 of the C-arm 16 to obtain various two-dimensional images along different planes in order to generate representative two-dimensional and three-dimensional images.

When the x-ray source 18 generates the x-rays that propagate to the x-ray receiving section 20, the radiation sensors 24 sense the presence of radiation, which is forwarded to the C-arm controller 28, to identify whether or not the imaging device 12 is actively imaging. This information is also transmitted to a coil array controller 48, further discussed herein. Alternatively, a person or physician may manually indicate when the imaging device 12 is actively imaging or this function can be built into the x-ray source 18, x-ray receiving section 20, or the control computer 28.

Figure 3B:
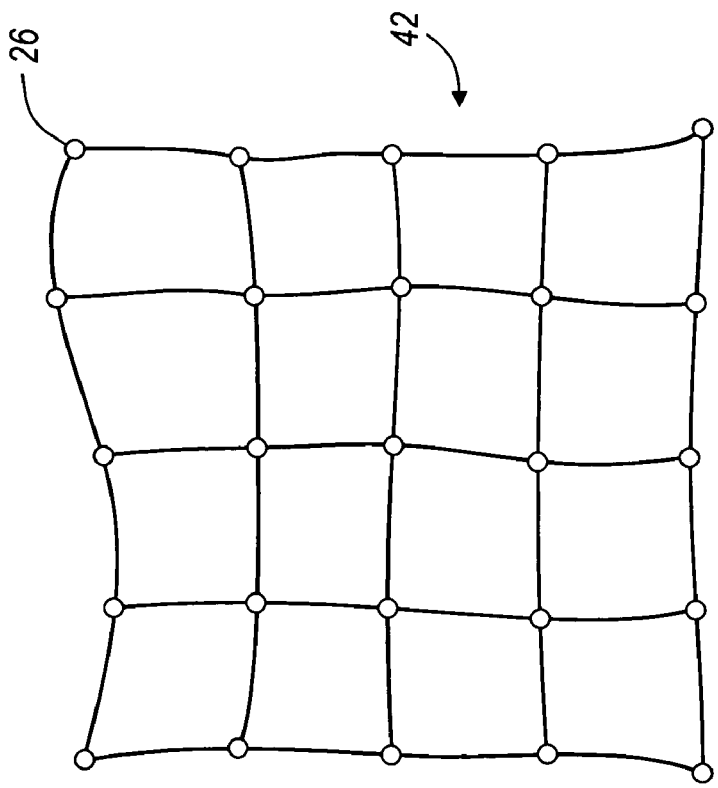
FIGS. 3A and 3B are diagrams representing undistorted and distorted views from a fluoroscopic imaging device.
Figure 3A:
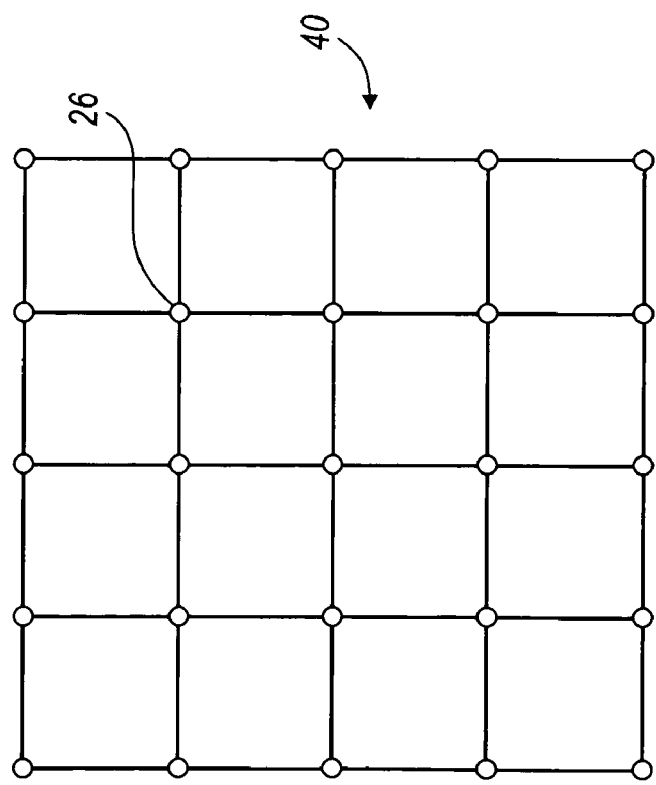

The optional imaging device 12, such as the fluoroscopic C-arm 16, that do not include a digital receiving section 20 generally require the optional calibration and/or tracking target 22. This is because the raw images generated by the receiving section 20 tend to suffer from undesirable distortion caused by a number of factors, including inherent image distortion in the image intensifier and external electromagnetic fields. An empty undistorted or ideal image and an empty distorted image are shown in FIGS. 3A and 3B, respectively. The checkerboard shape, shown in FIG. 3A, represents the ideal image 40 of the checkerboard arranged calibration markers 26. The image taken by the receiving section 20, however, can suffer from distortion, as illustrated by the distorted calibration marker image 42, shown in FIG. 3B.

Intrinsic calibration, which is the process of correcting image distortion in a received image and establishing the projective transformation for that image, involves placing the calibration markers 26 in the path of the x-ray, where the calibration markers 26 are opaque or semi-opaque to the x-rays. The calibration markers 26 are rigidly arranged in pre-determined patterns in one or more planes in the path of the x-rays and are visible in the recorded images. Because the true relative position of the calibration markers 26 in the recorded images are known, the C-arm controller 28 or the work station or computer 34 is able to calculate an amount of distortion at each pixel in the image (where a pixel is a single point in the image). Accordingly, the computer or work station 34 can digitally compensate for the distortion in the image and generate a distortion-free or at least a distortion improved image 40 (see FIG. 3A). A more detailed explanation of exemplary methods for performing intrinsic calibration are described in the references: B. Schuele, et al., "Correction of Image Intensifier Distortion for Three-Dimensional Reconstruction," presented at SPIE Medical Imaging, San Diego, Calif., 1995; G. Champleboux, et al., "Accurate Calibration of Cameras and Range Imaging Sensors: the NPBS Method," Proceedings of the IEEE International Conference on Robotics and Automation, Nice, France, May, 1992; and U.S. Pat. No. 6,118,845, entitled "System And Methods For The Reduction And Elimination Of Image Artifacts In The Calibration Of X-Ray Imagers," issued Sep. 12, 2000, the contents of which are each hereby incorporated by reference.

While the optional imaging device 12 is shown in FIG. 2, any other alternative 2D, 3D or 4D imaging modality may also be used. For example, any 2D, 3D or 4D imaging device, such as isocentric fluoroscopy, bi-plane fluoroscopy, ultrasound, computed tomography (CT), multi-slice computed tomography (MSCT), magnetic resonance imaging (MRI), high frequency ultrasound (HIFU), positron emission tomography (PET), optical coherence tomography (OCT), intravascular ultrasound (IVUS), ultrasound, intra-operative CT, single photo emission computed tomography (SPECT), planar gamma scintigraphy (PGS), or MRI may also be used to acquire 2D, 3D or 4D pre- or post-operative and/or real-time images or image data of the patient 14. The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities. A more detailed discussion on optical coherence tomography (OCT), is set forth in U.S. Pat. No. 5,740,808, issued Apr. 21, 1998, entitled "Systems And Methods For Guilding Diagnostic Or Therapeutic Devices In Interior Tissue Regions" which is hereby incorporated by reference.

Image datasets from hybrid modalities, such as positron emission tomography (PET) combined with CT, or single photon emission computer tomography (SPECT) combined with CT, could also provide functional image data superimposed onto anatomical data to be used to confidently reach target sights within the patient 14. It should further be noted that the optional imaging device 12, as shown in FIG. 2, provides a virtual bi-plane image using a single-head C-arm fluoroscope as the optional imaging device 12 by simply rotating the C-arm 16 about at least two planes, which could be orthogonal planes to generate two-dimensional images that can be converted to three-dimensional volumetric images. By acquiring images in more than one plane, an icon representing the location of an impacter, stylet, reamer driver, taps, drill, or other instrument, introduced and advanced in the patient 14, may be superimposed in more than one view on display 36 allowing simulated bi-plane or even multi-plane views, including two and three-dimensional views.

These types of imaging modalities may provide certain distinct benefits for their use. For example, magnetic resonance imaging (MRI) is generally performed pre-operatively using a non-ionizing field. This type of imaging provides very good tissue visualization in three-dimensional form and also provides anatomy and functional information from the imaging. MRI imaging data is generally registered and compensated for motion correction using dynamic reference frames (DRF) discussed further herein.

Positron emission tomography (PET) imaging is generally a pre-operative imaging procedure that exposes the patient to some level of radiation to provide a 3D image. PET imaging provides functional information and also generally requires registration and motion correction using dynamic reference frames.

Computed tomography (CT) imaging is also generally a pre-operative technique that exposes the patient to a limited level of radiation. CT imaging, however, is a very fast imaging procedure. A multi-slice CT system provides 3D images having good resolution and anatomy information. Again, CT imaging is generally registered and needs to account for motion correction, via dynamic reference frames.

Fluoroscopy imaging is generally an intra-operative imaging procedure that exposes the patient to certain amounts of radiation to provide either two-dimensional or rotational three-dimensional images. Fluoroscopic images generally provide good resolution and anatomy information. Fluoroscopic images can be either manually or automatically registered and also need to account for motion correction using dynamic reference frames.

Ultrasound imaging is generally an intra-operative procedure using a non-ionizing field to provide 2D, 3D, or 4D imaging, including anatomy and blood flow information. Ultrasound imaging provides automatic registration and does not need to account for any motion correction.

With continuing reference to FIG. 2, the navigation system 10 can further include an electromagnetic navigation or tracking system 44 that includes a localizer, such as a transmitter coil array 46, the coil array controller 48, a navigation probe interface 50, a device 52 (e.g. catheter, needle, or instruments, as discussed herein) and a dynamic reference frame 54. The dynamic reference frame 54 can include a dynamic reference frame member 80 and a removable tracking sensor 54a. Alternatively, the dynamic reference frame 54 can include a tracking sensor that is formed integrally with the dynamic reference frame member 80.

The transmitter coil array 46 may also be supplemented or replaced with a mobile localizer 46a. The mobile localizer 46a may be one such as that described in U.S. patent application Ser. No. 10/941,782, filed Sep. 15, 2004, and entitled "METHOD AND APPARATUS FOR SURGICAL NAVIGATION", herein incorporated by reference. As is understood the localizer array can transmit signals that are received by the dynamic reference frame 54, and the tracking sensors 58. The dynamic reference frame 54 and the tracking sensors 58 can then transmit signals based upon the received signals from the array.

It will be understood that the tracking system may be any appropriate tracking system and can include an optical tracking system with an optical localizer 47, illustrated in phantom such as the StealthStation® TRIA™ sold by Medtronic Navigation of Louisville, Colo. Other localization systems include acoustic, radiation, radar, infrared, etc. The optical localizer can transmit and receive, or combinations thereof. An optical tracking sensor 58a can be interconnected with the probe 66, or other portions such as the dynamic reference frame 54. As is generally known the tracking sensor 58a can reflect or transmit an optical signal to the optical localizer 47 that can be used in the navigation system 10 to navigate or track various elements.

Further included in the navigation system 10 may be an isolator circuit or assembly 55. The isolator circuit or assembly 55 may be included in a transmission line to interrupt a line carrying a signal or a voltage to the navigation probe interface 50. Alternatively, the isolator circuit included in the isolator box 55 may be included in the navigation probe interface 50, the device 52, the dynamic reference frame 54, the transmission lines coupling the devices, or any other appropriate location. The isolator assembly 55 is operable to isolate any of the instruments or patient coincidence instruments or portions that are in contact with the patient should an undesirable electrical surge or voltage take place.

It should further be noted that the entire tracking system 44 or parts of the tracking system 44 may be incorporated into the imaging device 12, including the work station 34 and radiation sensors 24. Incorporating the tracking system 44 may provide an integrated imaging and tracking system. Any combination of these components may also be incorporated into the imaging system 12, which again can include a fluoroscopic C-arm imaging device or any other appropriate imaging device.

The transmitter coil array 46 is shown attached to the receiving section 20 of the C-arm 16. It should be noted, however, that the transmitter coil array 46 may also be positioned at any other location as well. For example, the transmitter coil array 46 may be positioned at the x-ray source 18, within or atop the OR table 56 positioned below the patient 14, on siderails associated with the table 56, or positioned on the patient 14 in proximity to the region being navigated, such as on the patient's chest. The transmitter coil array 46 may also be positioned in the items being navigated, further discussed herein. The transmitter coil array 46 includes a plurality of coils that are each operable to generate distinct electromagnetic fields into the navigation region of the patient 14, which is sometimes referred to as patient space. Representative electromagnetic systems are set forth in U.S. Pat. No.

5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The transmitter coil array 46 is controlled or driven by the coil array controller 48. The coil array controller 48 drives each coil in the transmitter coil array 46 in a time division multiplex or a frequency division multiplex manner. In this regard, each coil may be driven separately at a distinct time or all of the coils may be driven simultaneously with each being driven by a different frequency. Upon driving the coils in the transmitter coil array 46 with the coil array controller 48, electromagnetic fields are generated within the patient 14 in the area where the medical procedure is being performed, which is again sometimes referred to as patient space. The electromagnetic fields generated in the patient space induce currents in a sensor 58 positioned on or in the device 52. These induced signals from the device 52 are delivered to the navigation probe interface 50 through the isolation circuit 55 and subsequently forwarded to the coil array controller 48. The navigation probe interface 50 may provide all the necessary electrical isolation for the navigation system 10. Alternatively, the electrical isolation may also be provided in the isolator box 55. Nevertheless, the isolator assembly 55 may be included in the navigation probe interface 50 or may be integrated into the device 52, and any other appropriate location. The navigation probe interface 50 can also include amplifiers, filters and buffers to directly interface with the sensors 58 in the device 52. Alternatively, the device 52, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled directly to the navigation probe interface 50.

Various portions of the navigation system 10, such as the device 52, the dynamic reference frame (DRF) 54, the probe 66, are equipped with at least one, and generally multiple, EM tracking sensors 58, that may also be referred to as localization sensors. The EM tracking sensor 58 can include one or more coils that are operable with the EM localizer array 44 or 44a. An alternative sensor may include an optical sensor, such as the optical sensor 58a, and may be used in addition to or in place of the electromagnetic sensor 58. The optical sensor may work with the optional optical array 47. One skilled in the art will understand, however, that any appropriate tracking sensor can be used in the navigation system 10. An additional representative alternative localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems.

In brief, the EM tracking sensor 58 on the device 52 can be in a handle or inserter that interconnects with an attachment and may assist in placing an implant or in driving a portion. The device 52 can include a graspable or manipulable portion at a proximal end and the tracking sensor 58 may be fixed near the manipulable portion of the device 52 or at a distal working end, as discussed herein. The tracking sensor 58 can include an electromagnetic sensor to sense the electromagnetic field generated by the transmitter coil array 46 that can induce a current in the electromagnetic sensor 58.

The dynamic reference frame 54 of the tracking system 44 is also coupled to the navigation probe interface 50 to forward the information to the coil array controller 48. The dynamic reference frame 54, according to various embodiments, may include a small magnetic field detector. The dynamic reference frame 54 may be fixed to the patient 14 adjacent to the region being navigated so that any movement of the patient 14 is detected as relative motion between the transmitter coil array 46 and the dynamic reference frame 54. The dynamic reference frame 54 can be interconnected with the patient in any appropriate manner, including those discussed herein. This relative motion is forwarded to the coil array controller 48, which updates registration correlation and maintains accurate navigation, further discussed herein. The dynamic reference frame 54 may be any appropriate tracking sensor used as the dynamic reference frame 54 in the navigation system 10. Therefore the dynamic reference frame 54 may also be optical, acoustic, etc. If the dynamic reference frame 54 is electromagnetic it can be configured as a pair of orthogonally oriented coils, each having the same center or may be configured in any other non-coaxial or co-axial coil configurations.

The dynamic reference frame 54 may be affixed externally to the patient 14, adjacent to the region of navigation, such as on the patient's cranium, etc., as shown in FIG. 2. The dynamic reference frame 54 can be affixed to the patient's skin, by way of a selected adhesive patch and/or a tensioning system. The dynamic reference frame 54 may also be removably attachable to fiducial markers 60 also positioned on the patient's body and further discussed herein. The dynamic reference frame 54 can also be connected to a bone portion of the anatomy. The bone portion can be adjacent, the area of the procedure, the bone of the procedure, or any appropriate bone portion.

Briefly, the navigation system 10 operates as follows. The navigation system 10 creates a translation map between all points in the image data generated from the imaging device 12 which can include external and internal portions, and the corresponding points in the patient's anatomy in patient space. After this map is established, whenever the tracked device 52 is used the work station 34 in combination with the coil array controller 48 and the C-arm controller 28 uses the translation map to identify the corresponding point on the pre-acquired image or atlas model, which is displayed on display 36. This identification is known as navigation or localization. An icon representing the localized point or instruments is shown on the display 36 within several two-dimensional image planes, as well as on three and four dimensional images and models.

To enable navigation, the navigation system 10 must be able to detect both the position of the patient's anatomy and the position of the device 52 or attachment member (e.g. tracking sensor 58) attached to the device 52. Knowing the location of these two items allows the navigation system 10 to compute and display the position of the device 52 or any portion thereof in relation to the patient 14. The tracking system 44 is employed to track the device 52 and the anatomy simultaneously.

The tracking system 44, if it is using an electromagnetic tracking assembly, essentially works by positioning the transmitter coil array 46 adjacent to the patient space to generate a low-energy magnetic field generally referred to as a navigation field. Because every point in the navigation field or patient space is associated with a unique field strength, the electromagnetic tracking system 44 can determine the position of the device 52 by measuring the field strength at the tracking sensor 58 location. The dynamic reference frame 54 is fixed to the patient 14 to identify the location of the patient in the navigation field. The electromagnetic tracking system 44 continuously recomputes the relative position of the dynamic reference frame 54 and the device 52 during localization and relates this spatial information to patient registration data to enable image guidance of the device 52 within and/or relative to the patient 14.

Patient registration is the process of determining how to correlate the position of the device 52 relative to the patient 14 to the position on the diagnostic or pre-acquired images. To register the patient 14, a physician or user 67 may use point registration by selecting and storing particular points from the pre-acquired images and then touching the corresponding points on the patient's anatomy with the pointer probe 66. The navigation system 10 analyzes the relationship between the two sets of points that are selected and computes a match, which correlates every point in the image data with its corresponding point on the patient's anatomy or the patient space. The points that are selected to perform registration are the fiducial markers or landmarks 60, such as anatomical landmarks. Again, the landmarks or fiducial points 60 are identifiable on the images and identifiable and accessible on the patient 14. The landmarks 60 can be artificial landmarks 60 that are positioned on the patient 14 or anatomical landmarks that can be easily identified in the image data. The artificial landmarks, such as the fiducial markers 60, can also form part of the dynamic reference frame 54, such as those disclosed in U.S. Pat. No. 6,381,485, entitled "Registration of Human Anatomy Integrated for Electromagnetic Localization," issued Apr. 30, 2002, herein incorporated by reference.

The system 10 may also perform registration using anatomic surface information or path information as is known in the art (and may be referred to as auto-registration). The system 10 may also perform 2D to 3D registration by utilizing the acquired 2D images to register 3D volume images by use of contour algorithms, point algorithms or density comparison algorithms, as is known in the art. An exemplary 2D to 3D registration procedure, is set forth in U.S. Ser. No. 10/644,680, entitled "Method and Apparatus for Performing 2D to 3D Registration" filed on Aug. 20, 2003, hereby incorporated by reference.

In order to maintain registration accuracy, the navigation system 10 continuously tracks the position of the patient 14 during registration and navigation. This is because the patient 14, dynamic reference frame 54, and transmitter coil array 46 may all move during the procedure, even when this movement is not desired. Alternatively the patient 14 may be held immobile once the registration has occurred, such as with a head frame. Therefore, if the navigation system 10 did not track the position of the patient 14 or area of the anatomy, any patient movement after image acquisition would result in inaccurate navigation within that image. The dynamic reference frame 54 allows the electromagnetic tracking device 44 to register and track the anatomy. Because the dynamic reference frame 54 is rigidly fixed to the patient 14, any movement of the anatomy or the transmitter coil array 46 is detected as the relative motion between the transmitter coil array 46 and the dynamic reference frame 54. This relative motion is communicated to the coil array controller 48, via the navigation probe interface 50, which updates the registration correlation to thereby maintain accurate navigation.

The navigation system 10 can be used according to any appropriate method or system. For example, pre-acquired images, atlas or 3D models may be registered relative to the patient and patient space. Generally, the navigation system allows the images on the display 36 to be registered and accurately display the real time location of the various instruments, such as the device 52, and other appropriate items, such as the pointer 66. In addition, the pointer 66 may be used to register the patient space to the pre-acquired images or the atlas or 3D models. In addition, the dynamic reference frame 54 may be used to ensure that any planned or unplanned movement of the patient or the receiver array 46 is determined and used to correct the image on the display 36.

With additional reference to FIG. 2, the dynamic reference frame 54 can be affixed to any appropriate portion of the patient 14, and can be used to register the patient to the image data, as discussed above. For example, when a procedure is being performed relative to a cranium 17, the dynamic reference frame 54 can be interconnected with the cranium 17. The dynamic reference frame 54 can be interconnected with the cranium 17 in any appropriate manner, such as those discussed herein according to various embodiments.

To obtain a maximum reference it can be selected to fix the dynamic reference frame 54 in each of at least 6 degrees of freedom. Thus, the dynamic reference frame 54 can be fixed relative to axial motion X, translational motion Y, rotational motion Z, yaw, pitch, and roll relative to the portion of the patient 14 to which it is attached. Any appropriate coordinate system can be used to describe the various degrees of freedom. Fixing the dynamic reference frame relative to the patient 14 in this manner can assist in maintaining maximum accuracy of the navigation system 10.

In addition the dynamic reference frame 54 can be affixed to the patient in such a manner that the tracking sensor portion thereof is immovable relative to the area of interest, such as the cranium 17. A head band may form a part of the dynamic reference from 54. Further, a stereotactic frame, as generally known in the art, can be attached to the head band. Such systems for tracking and performing procedures are disclosed in U.S. patent application Ser. No. 10/651,267, filed on Aug. 28, 2003, and incorporated herein by reference.

Although the navigation system 44, discussed above, can be provided in a plurality of ways and with a plurality of mechanisms it can be used to track the device 52. As discussed above the device can be a catheter 52 and can be any appropriate catheter and can include a tracking sensor such as the tracking sensor 58. The tracking sensor 58 included in the catheter 52 can be any appropriate tracking sensor and can be formed in any appropriate manner such as the catheters described in pending U.S. patent application Ser. No. 11/241,837, filed on Sep. 30, 2005, incorporated herein by reference. The catheter 52 can include the tracking sensors 58 at any appropriate position, such as near a distal end of the catheter 52. By positioning the tracking sensors 58 near the distal end of the catheter 52 knowing or determining a precise location of the distal end can be easily done. Determining a position of the distal end of the catheter 52 can be used to achieve various results, such as determining a precise position of the distal end of the catheter 52, a precise movement of the distal end of the catheter 52, or other appropriate purposes. It will be understood that knowing a position and moving the catheter 52 in a precise manner can be useful for various purposes, including those discussed further herein. Likewise, the catheter 52 can be directable according to various mechanisms and such as directing or pulling wires, directing or pulling signals, or any appropriate mechanism generally known in the art.

The catheter 52 can be used for various mechanisms and methods, such as delivering a material to a selected portion of the patient 14, such as within the cranium 17. The material can be any appropriate material such as a bioactive material, a pharmacological material, a contrast agent, or any appropriate material. As discussed further herein, the catheter can be precisely positioned, generally navigated, and otherwise used to achieve a protocol for positioning the material relative to the patient 14 in any appropriate manner, such as within the cranium 17.

Figure 4:
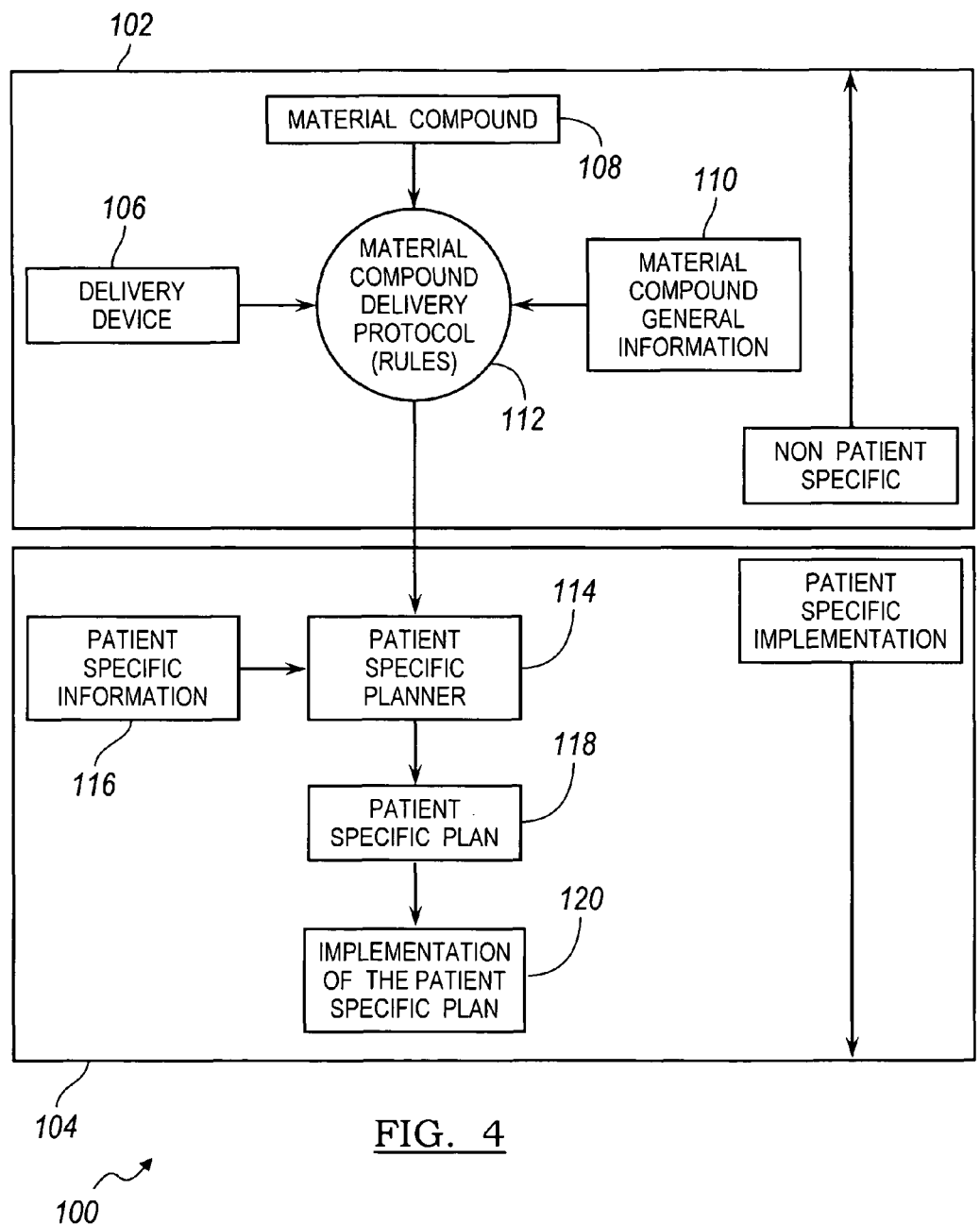
FIG. 4 is a flow chart illustrating a general overview of a patient specific planner system.

With reference to FIG. 4, an optimization system 100 is illustrated. The optimization system 100 can be a material delivery system, such as a pharmacological delivery system, a contrast agent delivery system, or any appropriate material delivery or therapy system and can be employed with the navigation system 10. The optimization system 100 can be used to achieve an optimal or best possible material delivery or therapy system for the patient 14 and can include patient specific information.

With continued reference to FIG. 4 and further reference back to FIG. 1, the optimization system 100 can generally include a non-patient or general portion block 102 and a patient specific block 104. The general block 102 can be similar to the Therapy Protocol in block 2 and include generally known or generally applicable information, such as the type, size, shape, and number of delivery devices employed in block 106 (e.g., the catheter 52), a known material compound 108 (e.g., a pharmacological or contrast material), and general material compound information in block 110. The general material compound general information can include information such as pharmacokinetics, a desired delivery position of the material compound, delivery, amount, rate of delivery, and other appropriate material compound general information.

The general information, such as the delivery device in block 106, material compound in block 108, and the material compound general information block 110, can be used to determine a material compound delivery protocol in block 112. The delivery protocol in block 112 can be any appropriate protocol and can include other factors, such as the rate of delivery, the position of delivery, the positioning of the delivery device, the concentration of the material compound, and include the material compound general information.

The various blocks in the non-patient specific block 102, such as the material compound delivery protocol in block 112, can be applied to a specific patient, such as the patient 14. Therefore, the material compound delivery protocol in block 112 can be input into the patient specific block 104 such as a patient specific planner block 114, which can be similar to the Patient Plan Optimizer in block 4. Various patient specific information from block 116, which can be similar to the Patient Specific Information in block 3, can also be input into the patient specific planner in block 114. Patient specific information can include patient specific images (e.g., MRI, image data, PET image data, etc.) that can be provided by the imaging device 12, patient malady, prior patient history, and other appropriate patient specific information that can assist in the patient specific planner in block 114, as discussed further herein.

The patient specific planner in block 114, can then be used to achieve or obtain a patient specific plan in block 118, which can be similar to the Proposed Plan in block 5. The patient specific plan in block 118 can be any appropriate patient specific plan, including those discussed herein. For example, the patient specific plan can include a selected or proposed path of the catheter 52, a size of the catheter 52, and any other appropriate information as part of the patient specific plan 118. Finally, implementation of the patient specific plan can be achieved in block 120, which can be similar to the Plan Implementation block 6. The implementation of the patient specific plan can be manual, navigated (such as with the use of the navigation system 10), automatic, or any other appropriate manner. Nevertheless, it will be understood that the patient specific plan determined in block 118 can be implemented in any appropriate manner in block 120, including those discussed further herein.

As schematically illustrated in FIG. 4, a method and process can be used to deliver a therapy to a patient. Various non-patient specific information and patient specific information and implementation can be provided and used to achieve such a result. The following description, although being merely exemplary, describes a system and apparatus that allows for creating and implementing a patient specific plan of producing or providing a therapy that can include patient specific information and general non-patient specific information.

Figure 5:
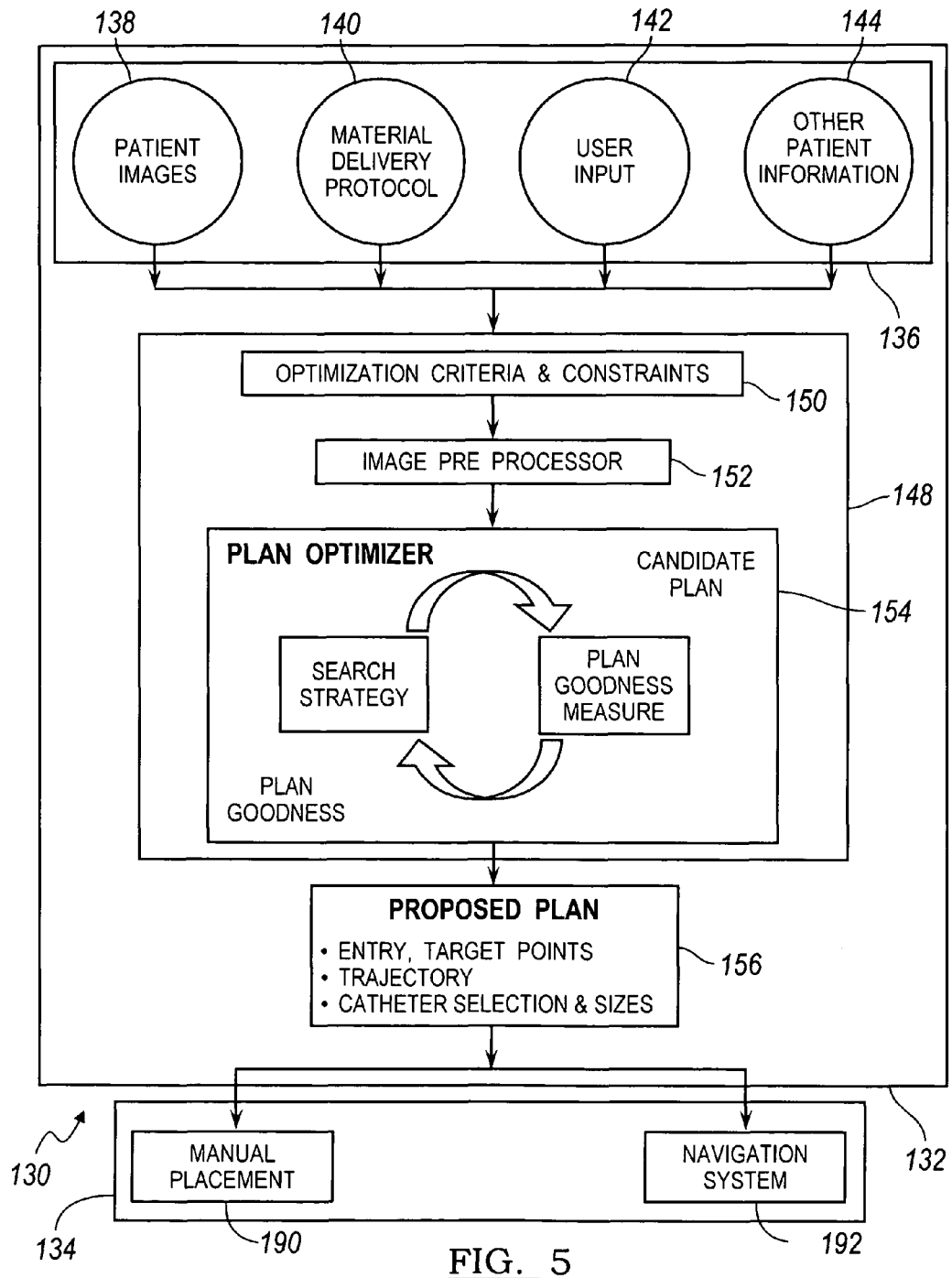
FIG. 5 is a flow chart illustrating a more detailed application of a patient specific planner.

Turning to FIG. 5, a planning and implementation process 130 is illustrated. The process 130 can generally be referred to as an optimization process and implementation and includes the same basic elements as the process 100. Generally, block 132 is a process or planning step while block 134 includes implementation steps that can either be sequential or divergent, as discussed further herein. The process in block 132 can be performed by any appropriate system, such as the work station 34 or the optimization processor 39. It will be understood that the optimization processor 39 can be a separate processor or integrated with the workstation 34.

With reference to the planning step in block 132, various inputs can be provided in input block 136. A first input can include patient images 138, and can include patient specific information as in block 116. The patient images 138 can be any appropriate image data, such as MRI image data, x-ray image data, fluoroscopic image data, or the like and can be created with the imaging system 12. For example, with reference to FIG. 6, an image data, such as three-dimensional image, 99 of a cranium 17 can include indications of the surface of the skull or skin 101 and various brain structures 103.

The image data from the image 99 can be any appropriate image data and can be stored in any appropriate location, such as in the navigation system 10, including the work station 34. The image data can be manipulated with the navigation system 10 (i.e. the work station 34) or the optimization processor 39 as is generally understood in the art. For example, the image data from the image 99 can be used to navigate various instruments, such as the catheter 52, relative to structures and portions in patient space relative to the image 99. It will be understood that although the following examples may be described in relation to the cranium 17, illustrated in the image data 99, any appropriate procedure can be performed based on various protocols. The various protocols could be any appropriate protocols that may be developed based upon the particular material to be delivered, procedure to be performed, etc. Various protocols that can be used include those described in Table 1 herein.

Returning to FIG. 5, a material delivery protocol in block 140 can also be a part of the input block 136, which can include information similar to the material compound delivery protocol in block 112, FIG. 4. The material and delivery protocol can be any appropriate protocol and can include any appropriate information. For example, a protocol can be developed to treat various diseases, injuries, maladies, or the like. A protocol can be created or used for brain cancer treatment, such as intra-tumor or para-tumor treatment with a particular material. The protocol can include the size of the catheter, a placement of a catheter, a turning radius of various catheters, a delivery rate of a catheter, a drug to be used, a timing or placement of the catheter and delivery of a drug, a volume of drug to be delivered, number of delivery points or number of catheters, and any other appropriate protocol information. The protocols can be developed for general procedures, such as drugs, a particular malady or the like and be applied generally to a patient population.

Various patient specific information or data can also be applied, as discussed herein, to create a patient specific plan or optimized patient specific plan. It will be understood that the following discussion may relate generally to a brain cancer protocol, with relation to image data 99, but any other appropriate protocols may be used or developed. For example, Table 1, included below, describes several protocols that relate to various therapies and procedures and each of the protocols can be input in block 140 as one skilled in the art will understand. The protocol inputted can be used to determine the positioning of a catheter instrument, a path of a catheter instrument, a material delivery rate, and material delivery location, or any other appropriate protocol information.

TABLE 1

| Therapy/Procedure | General Protocol |
|---|---|
| Brain cancer intratumoral and peritumoral treatment with IL13-PE38QQR | Optimal catheter placement considers: 1) depth from brain surfaces and intervening brain structures along trajectory of catheter and 2) tumor resection cavity proximity<br>Scoring criteria for catheter positioning assessment<br>1) Catheter $\geqq 2.5$ cm from brain surface or deep sulcus or resection cavity wall, if applicable (criteria A)<br>2) Catheter tip $\geqq 0.5$ cm from pial or ependymal surfaces (criteria B)<br>3) Catheter tip $\geqq 0.5$ cm from resection cavity walls (criteria C)<br>Note: Also placing catheter 2-4 days after resection improves placement accuracy. |
| Should rotator cuff repair catheterization | Placement: subacromial space through the anterior deltoid.<br>Avoid: cephalic vein, arthroscopic portals, incision site<br>Hazard: fluid leakage when patient is supine if catheter placed through posterior deltoid. |
| Catheterization for Anesthetic: Shoulder rotator cuff-intra-articular labral or capsular repairs | Placement: glenohumeral joint through the rotator interval |
| Catheterization for Anesthetic: Knee anterior cruciate ligament reconstruction | Placement: Intra-articular or at patellar tendon donor site |
| Catheterization for Anesthetic: Hamstring reconstruction | Placement: Intra-articular |
| Parenteral Nutrition using CV catheter | Catheter type: single-lumen preferred to multiple lumen to minimize risk of infection |
| Monitoring Central Venous (CV) Pressure | Regression relationship of patient age, height and weight with level of thoracic vertebra as indicator of optimal catheter depth (tip location) |
| Central Venous Catheter placement | Critical clinical variables: 1) catheter type 2) insertion site 3) patient's body habitus 4) intended use of catheter<br>Catheter Location: generally position with distal tip in the SVC, occasionally (hemodialysis or pheresis catheter) necessary to position in upper right atrium.<br>Landmark: trachobronchial angle indicator of SVC and SVC atrial junction.<br>Acceptable range of movement: 2-3 cm<br>Clinical variables to predict/limit movement: insertion site & patient's body habitus.<br>Safest insertion site: right internal jugular vein<br>Greater injury risk: left-sided catheter, catheter tip against vascular wall. |
| Pulmonary artery catheter placement | Evidence of correct placement: 1) 125 mL or more of air needed to obtain wedge tracing 2) PA catheter centimeter marking moved 1 cm or less at the introducer hub |
| Peritoneal Dialysis Catheter | Double cuff preferred over single cuff.<br>Insertion deep in rectus muscle or abutting preperitoneal fascia.<br>Downward directed exit.<br>Use pre-shaped arcuate catheter, implanted in an like-shaped tunnel.<br>Laparascopic insertion for complex situations; else bedside or ambulatory percutaneous placement acceptable. |
| Peritoneal Dialysis Catheter (pediatric) | Cuffs: Single preference, extra-peritoneal position, anchored in fascia.<br>If $2^{nd}$ cuff, 1.5-2.0 cm from exit site.<br>Exit site: lateral or downward direction. |

TABLE 1-continued

| Therapy/Procedure | General Protocol |
|---|---|
| | Omentectomy afterwards.<br>Patient-specific bicarbonate concentrations dependent on treatment modality (automated PD, continuous Ambulatory PD, automated PD with daytime dwell). |
| Dialysis or infusion of irritant/hypertonic fluids | Placement: Luminal opening in as large a vessel as possible.<br>Avoid: keep outside heart and avoid perforation and cardiac tamponade. Possibly avoid area above right atrium. |
| Gastrointestinal Drug Delivery | Consideration of specific characteristics of alimentary canal segments for drug therapy:<br>Anatomic characteristics (surface area, epithelium, mucosa, venous & lymphatic drainage)<br>Physiologic attributes (absorption pathways, pH, motility, transit time, enzymes)<br>Biochemical activities (endogenous, secretion, pH, gut flora, enzymes)<br>Mechanical activities (mucus, water coating layers)<br>Immunological characteristics (antigen stimulation at epithelial surface) |
| Contrast medium dosing for medical imaging | Patient parameters (weighting value undefined):<br>patient weight<br>patient hydration<br>kidney function<br>cardiac status<br>circulation transit time<br>vein status,<br>vessel diameter<br>length of scanning<br>catheter size or connector tube diameter |

The therapy protocols referenced in block 2, 112, or 140 and provided in Table 1 can be pre-planned or determined from various sources. Generally, the therapy protocols can be protocols that have been developed based upon experience of providing therapies to a population of patients. Also, one skilled in the art will understand that the therapy protocols and evaluations, in Table 1, may be an oversimplification. The exemplary protocols are presented as reasonable for illustrative purposes, but an actual evaluation may likely be much more quantitative in nature. Further, the plan goodness value, as discussed herein, and be any quantitative value based on selected criteria. Any of the therapy protocols is a set of rules that can be followed to achieve an optimal result. The Plan Optimizer in block 4, 114, and 154 is able to determine how to achieve the therapy protocol, or most closely to the therapy protocol, in the particular patient 14.

Returning to FIG. 5, a user input in block 142 can also be input in block 136. User input can be any appropriate input information, such as instruments available, user knowledge, or the like. User inputs can also include device specific information such as a turning radius, volume, etc. Finally, patient information can be inputted in block 144, such as information other than image information. Other patient information can include acceptable entry locations, pharmacological allergies, previous procedures, wound sites, weight, sex, and any other appropriate information. The user input block 142 and other patient information input block can include information that is similar to the patient specific information in input block 116.

The input information from block 136 can be input into an appropriate system 148. The input systems can include various systems such as touch screens, keyboards, etc. The system 148 (similar to the patient specific planner of block 114) can include a processor, such as a computer processor, a microprocessor, or any other system. The processor can include the work station 34 or it can be the processor system 39. It will be understood that the system 148 can use the input data from block 136 to create or output a proposed plan in block 156, as discussed herein, to be implemented by or with the assistance of the navigation system 10 or manually without the assistance of a navigation system. Therefore, the processor 148 need not be integrated with the navigation system 10, but can be integrated therewith for various reasons.

The system 148 can also generally be a substantially automatic system. The system 148 can be able to execute a computer readable or executable program based upon various algorithms discussed further herein, and as generally understood in the art. It will be understood that one skilled in the art can create a processor executable program, based upon the algorithms discussed herein, to determine an optimal or proposed plan based upon the input from block 136.

The system 148 can also include various modules, such as hardware modules. These can include generally known systems, such as memory systems, processor systems, bus systems, and the like. The various hardware components will now be discussed herein as in generally known in the art. Various program modules or algorithm modules can also be provided as computer executable programs. The various exemplary modules can include an optimization criteria and constraints module 150, an imager pre-processor module 152, a plan optimizer module 154, and a proposed plan module 156. The various modules 150-156 can be understood to be separate modules, as illustrated here or can also be integrated into a single module that can be executed by a processor, as is generally understood in the art. The separation of the modules is provided for clarity of the current discussion and is not necessarily required for operation of the system.

Figure 7:
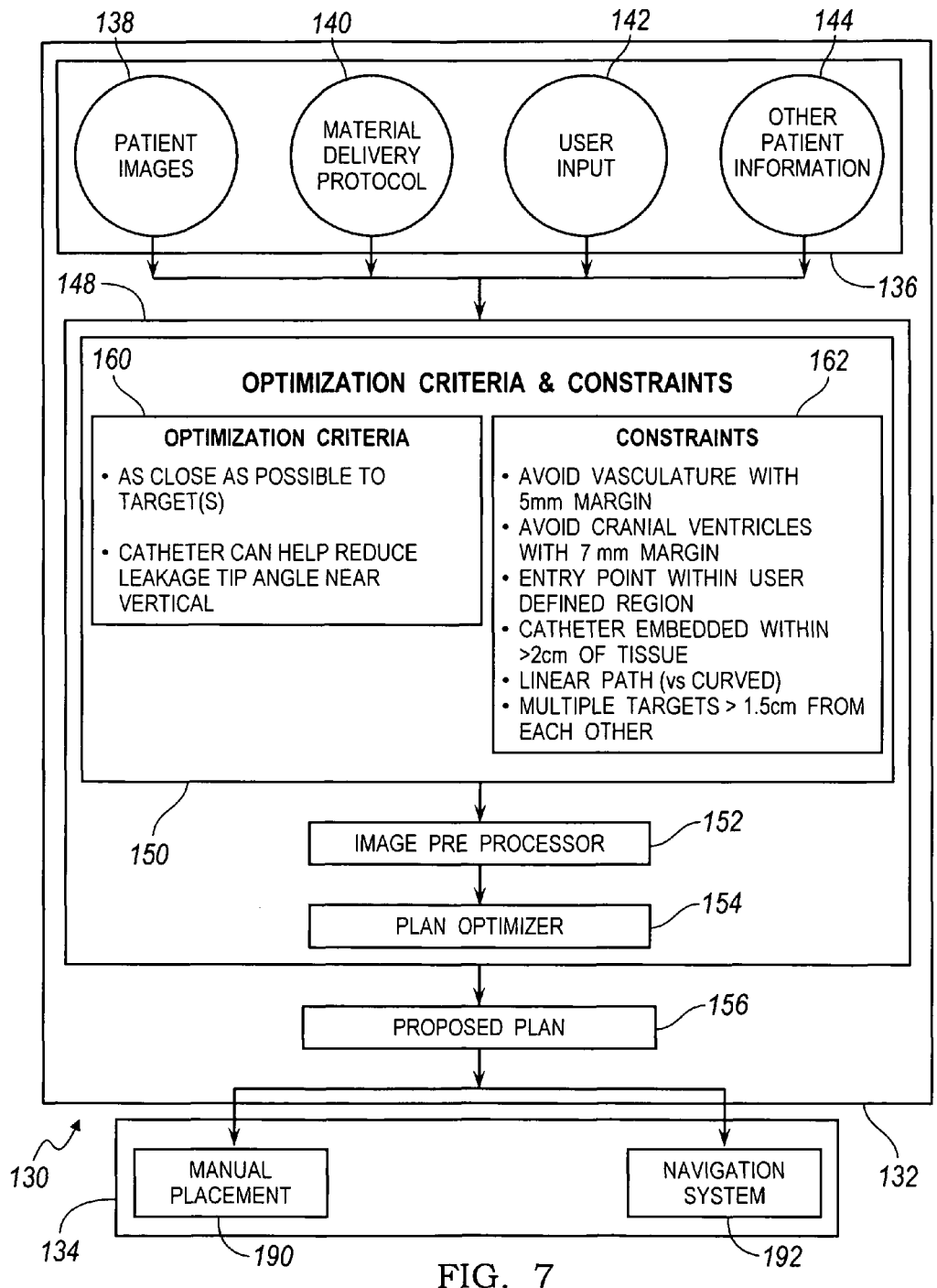
FIG. 7 is a flow chart specifically illustrating optimization criteria and constraints.
Figure 8:
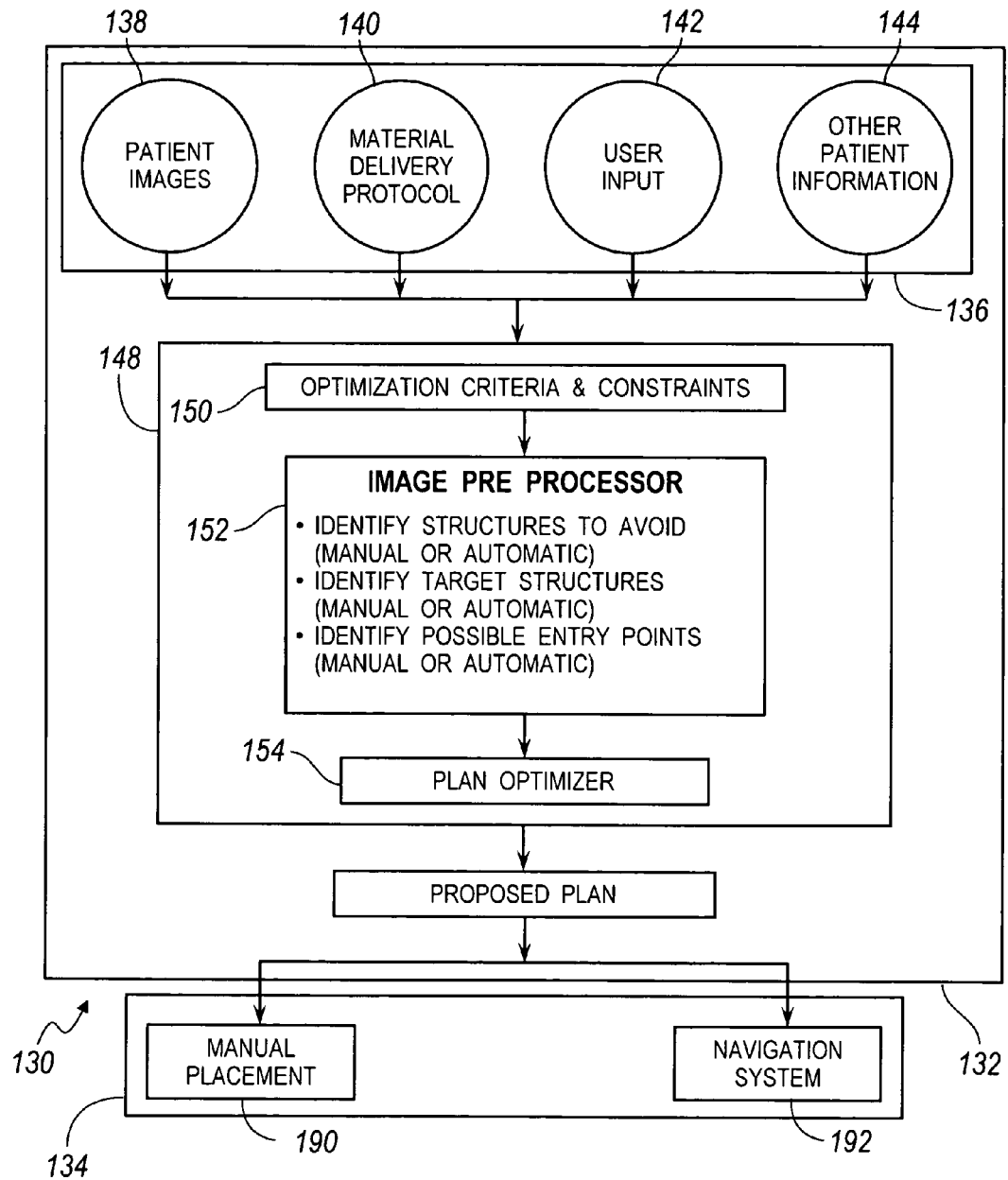
FIG. 8 is a flow chart specifically illustrating an image pre-processor system.

With reference to FIG. 7, the optimization criteria and constraints module 150 can include various sub-modules, such as an optimization criteria module in block 160 and a constraints module in block 162. The optimization criteria in block 160 can include various criteria that could be weighted to be used to achieve or assist in achieving a selected result. The constraints module in block 162 can provide stop or limit criteria that can be used to completely disregard various proposed plans.

The optimization criteria in block 160 can include any appropriate optimization criteria. For example, optimization criteria can include positioning an instrument, such as a catheter, as close as possible to a target or targets. Further optimization criteria can include positioning the catheter at a selected orientation, such as near vertical or vertical. Other optimization criteria may include the size of the catheter, projected speed of positioning, ease of forming an incision or entry port, or other appropriate optimization criteria. Generally, optimization criteria can include criteria that can be weighted for determining an appropriateness or optimization of a particular plan, as discussed further herein. Therefore, it will be understood that the optimization criteria can be determined and weighted for use in an algorithm to determine an optimized plan. For example, the closeness of a catheter to a target can be weighted four times as much as the catheter tip being substantially vertical. Therefore, during the plan optimization step, the plan that achieves the catheter closest to the target may be deemed or determined to be more optimized than one that positions the catheter that has a nearly vertical orientation. It will be understood that any one or a plurality of optimization criteria can be weighted and each can be weighted based upon various mechanisms. For example, the optimization criteria may be determined and weighted based upon the material delivery protocol, which is input into the system 148. The optimization criteria in block 160 can be used in the plan goodness measure block 182 to create a plan goodness value for a candidate plan.

In addition, constraints in block 162 can also be part of the optimization criteria and constraints block 150. The constraints can be any appropriate constraints and can also be included as either patient specific data or as part of the material delivery protocol. Various constraints can include positioning or avoiding vasculature by a selected margin, avoiding cranial ventricles by a particular margin, having an entry port within an entry region defined by a user, insuring a position of the device 52 (e.g. the catheter 52) within selected tissue, a desired or selected path, or the position or designation of several targets.

For example, with reference to the protocol described in Table 1 for the brain cancer treatment, positioning a catheter greater than or equal to 2.5 cm from the brain surface or cavity wall, having the catheter tip greater than or equal to 0.5 cm from the pial or ependeymal surfaces, or having the catheter tip greater than 0.5 cm from the resection cavity walls can all be constraint criteria. The constraint criteria can be provided as the criteria at which the system 148 will completely eliminate or ignore a candidate plan. In addition, for example, a particular path, such as a linear path can be provided as a constraint. Therefore, any path that may be planned or determined that is not linear can be immediately eliminated without being provided as a proposed plan.

It will be understood, however, that the optimization criteria can be the constraint criteria in a greater sense. For example, with reference to the brain cancer protocol, a constraint can be that the catheter is at least 2.5 cm from the brain surface or resection cavity wall. However, this can also be used as an optimization criterion in that a plan that allows for the catheter to be positioned even greater than 2.5 cm may be weighted more than a plan that is only 2.5 cm from the selected position. It will also be understood that the weights may change depending upon the value of the position of the catheter. For example, a plan that allows the catheter to be 3 cm from the brain surface can be weighted X, while a plan that allows for the catheter to be positioned 4 cm from the brain surface can be weighted 2X. Therefore, the greater or further a plan moves the planned path or position of the catheter from the constraint can be weighted even greater than a plan that merely achieves or does not reach one of the constraint criteria.

As discussed above and further herein, the proposed plan in block 156 can be any appropriate plan and can be similar to the patient specific plan from block 118. Therefore, the plan can include a final position of an instrument, a path to reach the final destination, and various other plan portions. The plan from block 156 can be displayed on the image data, as exemplary illustrated in FIG. 6. Therefore, the optimization criteria and the constraints can include criteria that relates to any of these portions of the plan. For example, the path can be part of the plan and can be provided as both a constraint criterion and an optimization criterion. Further, a final destination, such as a particular anatomical location, can be both a constraint criterion and an optimization criterion. For example, a final destination can be known and determined in the patient specific image data and a constraint criterion could be that the catheter must be no further than 3 cm from the final target. However, this could also be used in the optimization criteria and that the closer to the catheter it is to the final destination or selected destination, the more highly weighted or better scored the plan is.

The optimization criteria and constraints can be provided for any appropriate purpose. For example, a plan that is more optimized or has a high plan goodness value can be better than a plan with a lower plan goodness value. Further, the various optimization criteria and constraints can be used to preprocess the image data in block 152. In block 152, the image processor, which can be an executable program by a processor to use the image data, such as from the image 99 in FIG. 6, that can be obtained from the imaging system 12, to achieve or determine appropriate information. For example, the image pre-processor can determine the target location, such as a tumor 170 in the brain 156. It will be understood that any appropriate target can be determined depending upon the appropriate procedure, such as a subacromial space through the anterior deltoid in a shoulder rotator cuff repair catheterization, intra-articular or at patellar tendon donor site for catheterization for anesthetization of a knee for an ACL replacement or any other appropriate target location. Nevertheless, the example discussed herein can include the tumor 170 as the final target. The exemplary procedure may also include pre-processor identifying the ependymal or pial surfaces per the Therapy Protocol described in Table 1.

Also, the image pre-processor can be substantially automatic or manual, as discussed above in regards to registration and anatomical mapping. For example, the image preprocessor can determine the location of the tumor 170 through various known mapping techniques based upon the outline of the tumor 170, various physiological features that can be illustrated or determined in image data from MRI data, SPECT data, PET data, or the like. In addition, a manual determination or validation of the location of the tumor 170 can be used. Alternatively, the determination of the position of the tumor 170 can be used substantially manual. For example, a user can determine a position of the tumor 170 to various techniques, such as reviewing the image data and inputting a specific location in the image data to a touch screen, keyboard input or other appropriate input methods. Nevertheless, the pre-processor can determine the target location, such as the tumor 170, to be used in the plan optimizer 154.

Further, the image pre-processor can be used to determine an appropriate entry site 172. The entry site can be determined or selected for various appropriate reasons, such as based upon prior procedures, based upon the location of the tumor 170, based upon the desire to avoid various structures, access to the underlying tissue or other appropriate reasons. Again, the access site 172 can be determined substantially only automatically, a mixture of automatic and manual, or substantially only manually. Further, the entry site 172 can be in part determined by the patient specific information. For example, the site 172 can be selected or at least various sites can be eliminated based upon prior procedures, defects in the patient's anatomy, structure in the patient's anatomy, or the like. Also, the image pre-processor can be used to determine various structures that are desired to be avoided. The structures to be avoided can be determined as part of the constraints that are determined in block 150. Therefore, if a constraint is used such as avoiding a various structure, such as a vein or other structure must be avoided, the image pre-processor can determine the structure in the image data 99. Again, the determination of the structure to be avoided can be substantially automatic, a mixture of automatic and manual, or substantially only manual.

Exemplary manual determination of a structure to be avoided can include selecting an area on the image data displayed on the display 36 to be avoided. Alternatively, prior image data of the patient 14 can be input. For example, prior image data or navigation data of prior procedures can be used by the system 148 to determine areas of the patient's 14 anatomy to be avoided. In any situation, however, structures can be identified in the anatomy to be avoided by a path or proposed plan in block 154.

With reference to the example for treating the brain tumor 170, various structures, such as the surface of the brain 174 can also be determined in the image data 99. Therefore, during the plan optimization or plan creation, the achievement of eliminating or not breaching one of the constraints or achieving an optimization can be determined. Further, for example, the pial or ependymal surfaces can also be determined in the image data 99 for use in the plan optimizer. Therefore, the image pre-processor in block 152 can be used to process the image data 99 input from block 138 into the system 148 to assist in determining various target locations, structures to be avoided, and other appropriate information.

It will be understood that the image data can be any appropriate image data and can actually include a plurality of image data types. For example, it may be that the image data 99 is a composite image data that includes image data from various sources that are able to illustrate or more easily show particular structures. Therefore, the image pre-processor in block 152 can also assist in compositing or compounding the image data to be used in determining the various features, such as the location of the tumor 170, the surface of the brain 174, or other appropriate information. It will also be understood that the image data can be composited substantially manually for use by the optimizer system 148.

Input by a user can be used by the plan optimizer 154, such as for a part or all of a selected path. Nevertheless, the path can also be generally completely determined by a processor, such as a computer processor. That is, a computer processor can execute the computer program based upon the various algorithms and instructions disclosed herein to produce a proposed plan. The path determined by the plan optimizer can be based upon the image data 99 to determine an entry point, a path, and a final destination of an instrument, such that the catheter 52.

Figure 6:
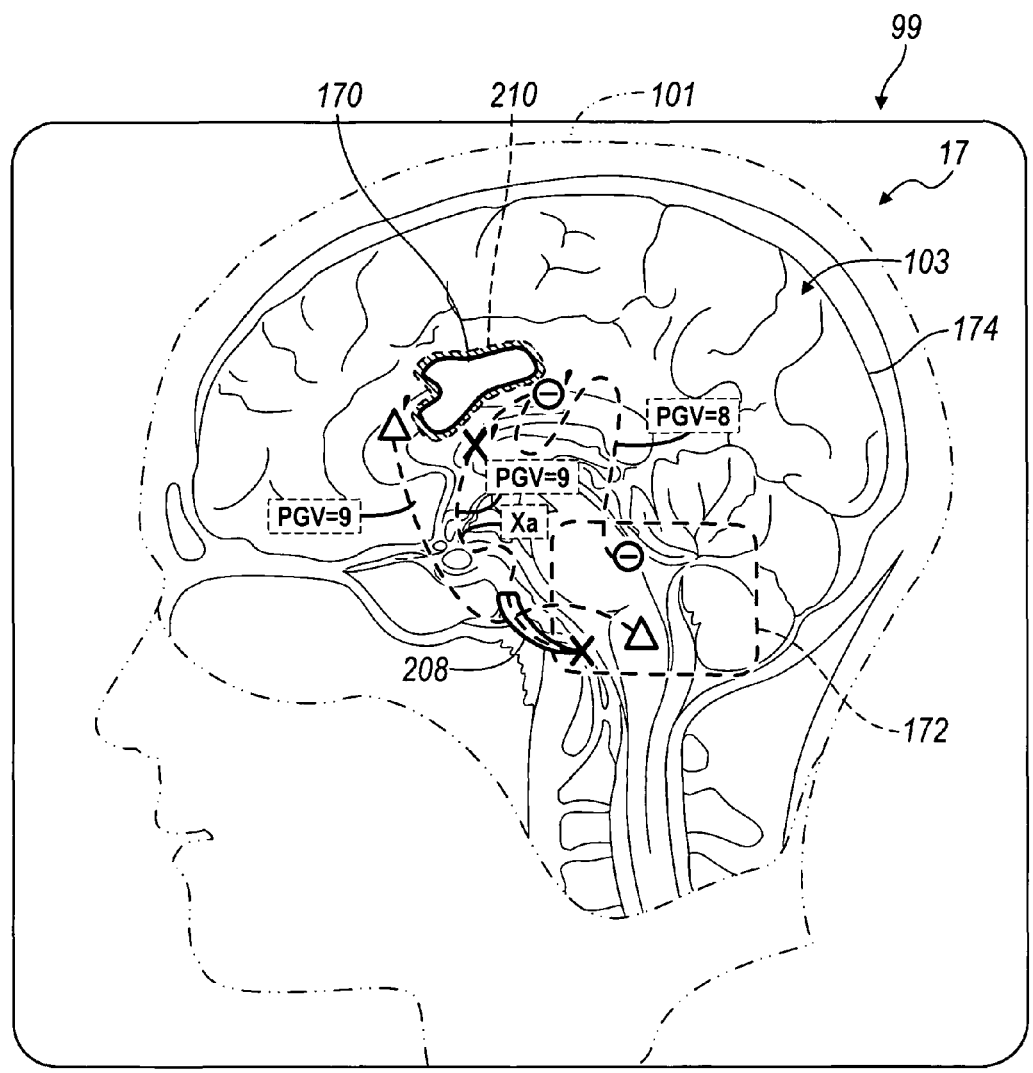
FIG. 6 is an illustrated detail view of a cranium representing image data.
Figure 9:
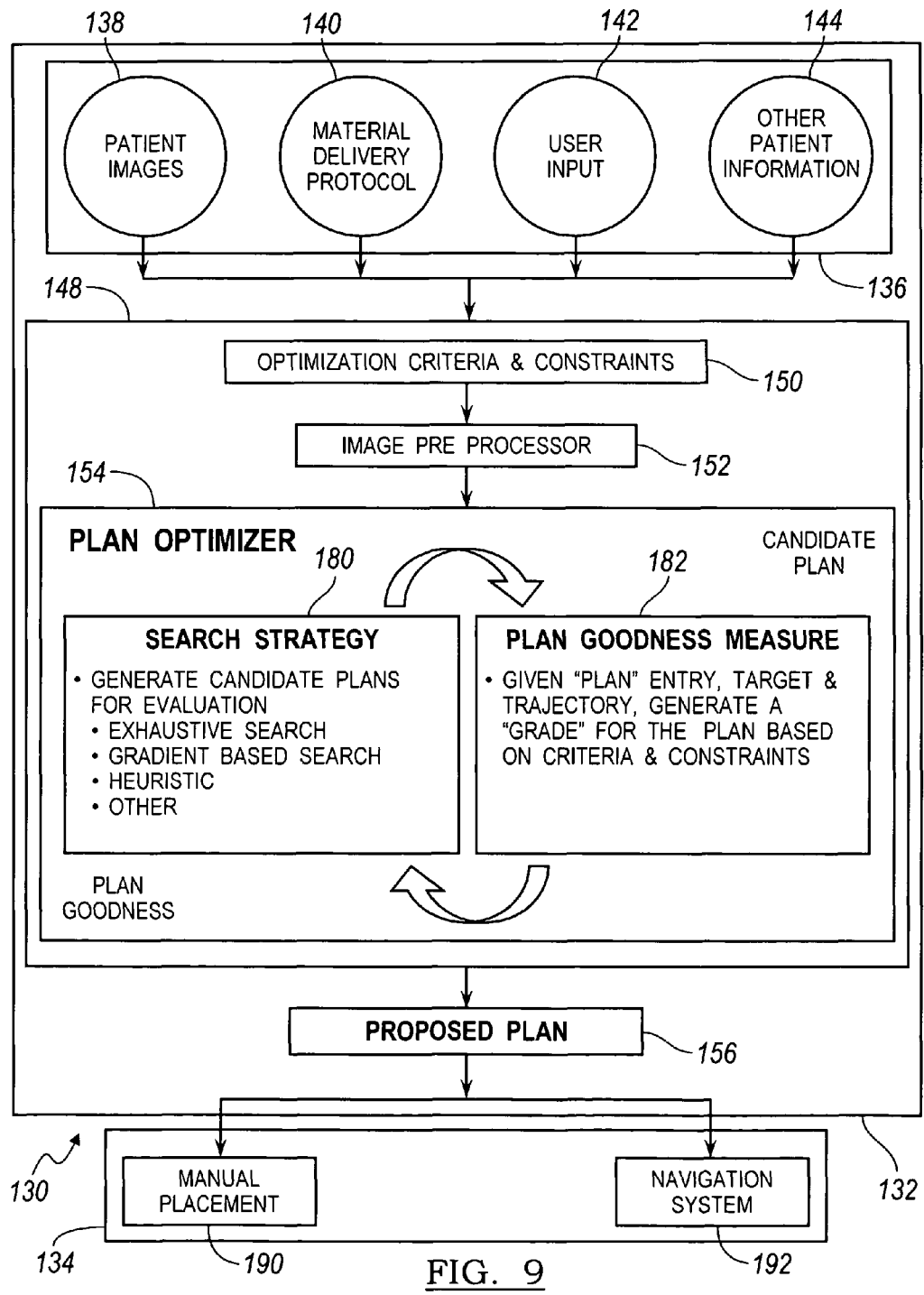
FIG. 9 is a flow chart illustrating a plan optimizer system.

With reference to FIGS. 6 and 9, various paths can be determined. The path can be a part of the candidate plan or proposed plan. It will be understood that other information, such as catheter size, may also be part of the proposed plan. Nevertheless, the proposed plan paths can be displayed on the display 34 relative to the image data 99.

For example, an entry point, such as entry point X, entry point Δ or entry point ⊖ can be determined within the general entry area 172. As discussed above, the tumor 170 can already be determined when the image pre-processor, which can be a part of or a separate processing system for the plan optimizer. Nevertheless, various final points, such as X', Δ' or ⊖' can also be determined. The various destination points can be determined prior to or after the various paths have been determined. The paths generally include X to X', Δ to Δ', and ⊖ to ⊖'. As illustrated in FIG. 6, each of the various paths can be different and be based upon the constraints and criteria inputted in the optimization criteria and constraints module 150.

For example, the plan having entry point X, destination point X' and path X-X' can be determined based upon the various search strategies. It will be understood that the search strategy can either be constrained or unconstrained, and that only a single search strategy can be used or dictated or the system can be allowed to use any appropriate search strategy. Nevertheless, the various structures to be avoided can be determined in the image pre-processor, the entry area 172 can be determined in the pre-processor, and the location of various constraints can also be determined in the image pre-processor.

Therefore, the plan optimizer 154 can use a search strategy 180 to determine various points through which a catheter can pass to achieve the destination X' from the entry point X. Therefore, the path X-X' can be a path that is determined based upon the search strategy and the various optimization criteria and constraints that have been put into the plan optimizer 154 to provide or plot a path to the brain tumor 170.

The search strategy can be any appropriate search strategy. Search strategies can include exhaustive searches, heuristic searches, gradient-based, etc. For example, an exhaustive search based upon the optimization criteria and constraints may determine every pixel in the image data that does not reach a constraint. The constraint may be those pixels that define anatomical structures to avoid. The exhaustive search may then map every possible path of continuously connected pixels to move from the entry point to a destination point. Each of these paths may be a candidate path which can be a part of a candidate plan. Various plans may include catheter size which may dictate different paths to create further candidate plans. The candidate plans found in the search strategy can then be give a plan goodness value in the goodness measure module 182.

One skilled in the art will understand that these and other search strategies may also be used. Various strategies may include those that create a first plan and then modify it only on the PGV to achieve a higher PGV. Various search strategies that may be used include those disclosed in or augmented from "Numerical Recipes in C, The Art of Scientific Computing", Second Edition. 1992, W.H. Press, S. A. Teukolsky, W. T. Vetterling, B. P. Flannery, Cambridge University Press, Cambridge or "Optimization and Industrial Experimentation", 1980, W. E. Biles, J. J. Swain, 1980. Wiley, N.Y. Also, various data mining or knowledge based search systems can be used in the search strategy module 180.

A candidate path can be produced from the search strategy that is then input into a plan goodness measure module 182. The plan goodness measure module 182 can then create a plan goodness measure which can include any appropriate measure, such as a particular grade or numerical value. The plan goodness measure can be based upon a scale of how good the candidate plan from the search strategy 180 achieves the optimization criteria. It will be understood that either in the search strategy module 180 or in the plan goodness measure module 182 that a candidate plan can be determined to be impossible. For example, all candidate plans can be input into the plan goodness module and a plan goodness measure can also include of "impossible" or a plan goodness values (PGV) of zero can be determined if the constraints from the constraints module 150 are breached. Alternatively, the search module 180 can be created so that breaching a constraint is not allowed as a candidate plan. Nevertheless, as a part of the plan goodness measure, the determination of whether a constraint has been breached can be determined.

Further, the various optimization criteria can be used, as weighted in module 150, to assist in creating a plan goodness value. The plan goodness value can be determined based upon the achievement of the various optimization criteria, such as a final position of the catheter 52, a closeness of the catheter 52 to the brain tumor 170, an entry point, an entry trajectory, a proposed time of reaching the final destination, or any other appropriate optimization criteria. The plan goodness measure modules 182 can therefore assign a plan goodness value to each of the candidate plans that are found in the search strategy module 180. As illustrated in FIG. 6, the various plans X-X', Δ to Δ', and ⊖ to ⊖' can be given various PGVs.

The above is, essentially, the main algorithm for creating the proposed plan in block 156. Various candidate plans can be determined or found in the search strategy in block 180. The candidate plans can be given a plan goodness value in the plan goodness measure module 182. Plans that are given extremely low or relatively low values can be disregarded by the plan optimizer 154, based upon or in lieu of plans that have higher PGVs. The search strategy in block 180 can then create further candidate plans based upon the previous candidate plans and their respective PGVs. In this way the plan optimizer 154 can determine the best candidate plans and make the proposed plans in block 156.

The plan optimizer 154 can create various plans that have an appropriate PGV. As exemplary illustrated in FIG. 6, the various plans can have PGVs of 9, 9, and 8, respectively. The various PGVs can include the appropriate threshold values above which plans can be proposed and below which plans may not be proposed. The PGVs can be based on any appropriate grading or goodness factors, such as the optimization criteria in block 160.

A plan or a plurality of plans that have an appropriate plan goodness value can then be proposed in block 156. The proposed plans can include various information, such as entry points, target points, trajectories, overall paths, catheter size selection, and any other appropriate information. Further, the various plans can be illustrated relative to image data, such as illustrated in FIG. 6. The final selection of a proposed plan can be achieved using any appropriate mechanism.

For example, the plan optimizer 154 can be designed to disregard all plans save for the best plan. If more than one plan includes the same plan goodness value, for example, X-X' and Δ to Δ' the plan optimizer 154 may apply a separate or more rigorous set of optimization criteria that can also be input into the plan optimizer 154 to create an augmented PGV. The proposed plan may then include only the single plan that has the highest augmented plan goodness value. Nevertheless, it may desirable, to various users, to make the final decision based upon prior knowledge, experience of the user, time available, instruments available, or any other appropriate information that may not be included in the plan optimizer module 154.

Therefore, it will be understood that various information, which can include patient specific or non-patient specific information, can be inputted into the process 148. As discussed above, various patient specific information can include a particular malady, patient image data, other patient information or user input (e.g., available catheter sizes, available time limits, available drug therapies, etc.). The process 148 can then be executed to determine a proposed plan in block 156. The process 148 can be carried out substantially automatically by various known mechanisms, such as a processor including a micro-processor generally known in the art. The processor can carry out a set of computer executable instructions that can be based upon the optimization criteria and constraints to determine various structures in the image data, and search for various plans and to determine a PGV based upon the various input. Therefore, a computer processor can be used to substantially create plans and select from the constructed plans to determine a most appropriate plan. This can allow a user to substantially carry out the plan based upon the known material delivery protocols from block 140 and various user and patient data from blocks 138, 142, and 144. The user can then carry out the plan from the proposed plan in block 156 without worry of various minutia, such as determining a path during a procedure, determining an appropriate position of the catheter 52 during the procedure, or various other details. The user can then focus the user's extensive knowledge and experience on the particular patient and patient goals.

The proposed plan from block 156 can then be implemented by a user according to various methods. For example, the implementation block 134 can include various implementation methods, such as, with reference to FIG. 5, manual placement in block 190 or navigated placement in block 192. The implantation block can be similar to the implementation of the patient specific plan from block 120. Manual placement in block 190 can include placing the catheter 52 substantially manually without any navigation instruments, such as the navigation system 10.

Manual placement of the catheter 52 can be based upon user knowledge, various intraoperative imaging techniques that do not use any navigation system, and other manual placement techniques. For example, the catheter 52 can be passed from the determined entry point to the determined final position point based upon movement of the catheter along a selected path that can be verified with various instruments, such as a fluoroscope or any other appropriate imaging system. Such manual placement can be selected for various techniques, such as in treating the brain tumor 170, delivering anesthesia or the like. For example, it may be selected to place the catheter substantially manually when delivering anesthesia or other materials to a large area, such as a knee, a shoulder, or the like. It may be selected, however, to use the navigation implementation in block 192 for smaller targets, more and more sensitive areas, such as the brain 156.

Figure 10:
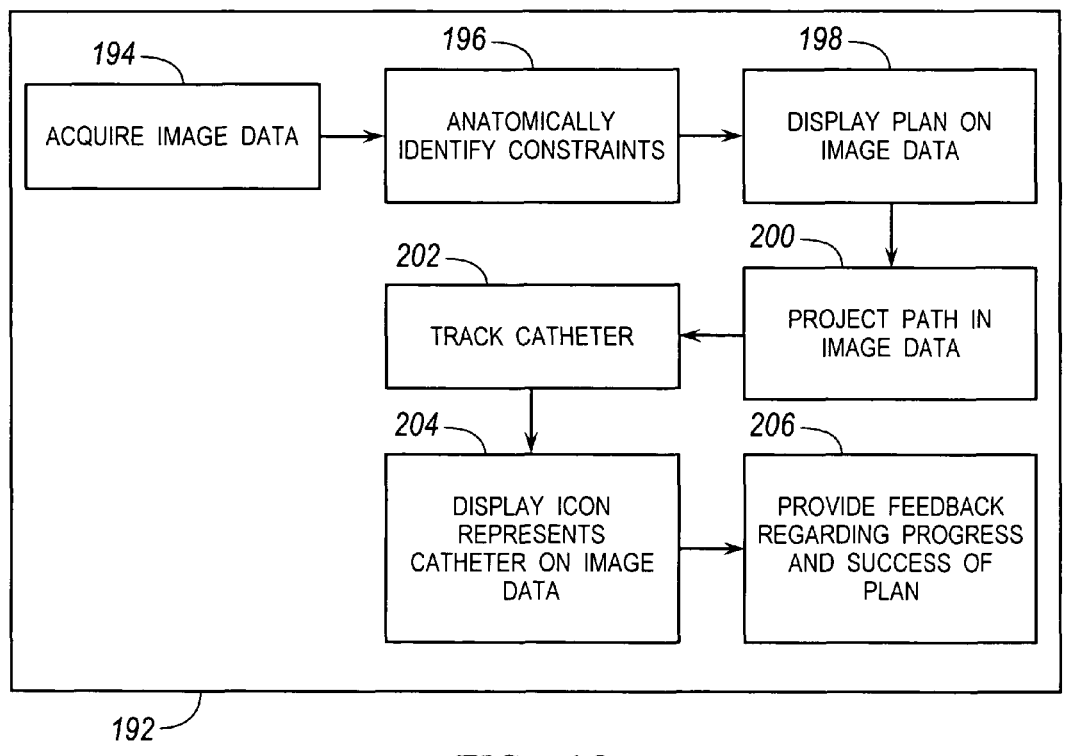
FIG. 10 is a flow chart illustrating a navigation implementation system.

The navigation implementation in block 192 can include various portions. With reference to FIGS. 10 and 6, the navigation implementation in block 192 will be described. It will be understood that the navigation implementation described herein is merely exemplary. For example, FIG. 6 includes the image data 99 of the cranium 17 of the patient 14. It will be understood that the navigation implementation 192 can be used for any appropriate procedure and navigation of a catheter relative to the cranium 17 is merely exemplary. One skilled in the art will understand that the various protocols described in Table 1 can be used to achieve various navigation implemented plans for various portions of an anatomy.

One skilled in the art will understand that the implementation in block 192 can be the final step in the optimized therapy planner 1 (i.e. 100 or 130). That is that a therapy protocol from block 2 (i.e. 140) can first be determined and input into the plan optimizer 4 (i.e. 154). The therapy protocol can be any appropriate protocol, such as those described in Table 1 above. As discussed above the therapy protocol can include both the constraints and the optimization criteria for a particular therapy, such as a drug delivery.

Other input can also be patient specific information or data, such as image data in block 138 or other patient specific information or user data, such as weight, sex, age, previous procedures, etc. (i.e. 3, 142, 144). The patient specific information can also be input into the Patient Plan Optimizer 4 (i.e. 154). The patient data can include the image data captured by the imaging device 12. Other user input in block 142 can also include device data, such as maximum or minimum turning radius, longevity, maximum or minimum delivery rates, etc.

Once the patient specific information and the therapy protocol haven been selected and provided to the system 148, which can include the optimization processor 39, the optimization process can occur. The process can include various steps such as determining the various constraints and optimization criteria from the therapy protocol or entered separately. Based on these constraints and optimization criteria the image data, and other patient specific information, can be pre-processed in the image pre-processor in block 152. The pre-processing can be used, as discussed above, to determine the location of a target and various anatomical features.

The plan optimizer in block 154 (i.e. 4 or 114) can use the therapy protocol (e.g. optimization criteria and constraints) and the patient specific information (e.g. image data) to determine candidate plans and proposed or optimized plans. The candidate plans can be determined based upon the various search strategies in block 180 and the input information. For example the plan optimizer 154 and search strategies 180 may take into account the working area available form the image data and the size catheters available for a drug delivery. These may also be used as constraints or optimization criteria by the plan optimizer 154, either input by a user or determined by the system. These search strategies can include any generally known search strategies. The candidate plans can then be graded or ranked in the Plan Goodness Measure module in block 182. The candidate plans can be graded based on the optimization criteria (e.g. achieving a goal, a distance from a selected location, proximity to a target location, duration of a procedure, planned drug delivery success, etc.) in the Plan Goodness Measure block 182. The various graded candidate plans can then be rejected or formed as one or many proposed plans in block 156. The proposed plans from block 156 can then be implemented in block 6 (i.e. 120 or 156). The implantation can be any appropriate implementation such as manual, navigated, or automatic (e.g. robotic).

The exemplary navigation implementation 192 can include acquiring image data in block 194, such as with the imaging system 12. The image data acquired in block 194 can include the patient images from block 158 or other image data. For example, the image data acquired in block 194 can include additional or new image data, which can be substantially similar to the image data 99 for assisting in carrying out the navigation implementation in block 192. The various constraints, such as anatomical constraints can be identified in block 196. The identification of the anatomical constraints in block 196 can be those produced or determined in the image pre-processor module 152. It will be understood that the navigation implementation in block 192 can be substantially integral with the process 148, particularly if the process 148 is a part of the navigation system 10. Nevertheless, the identified anatomical constraints in block 196 can be input from the module 152 if the systems are separate.

The image data and the proposed plan can then be displayed on an appropriate display, such as the display 36. The display 36 can display the image data and the plan, or multiple plans, relative to the image data 99. For example, FIG. 6 can be exemplary of the display 34 that includes both the image data 99 and one or more of the proposed plans X-X', Δ to Δ', and ⊖ to ⊖'. It will also be understood that more than one plan can be proposed and displayed for use during a procedure. The multiple plans can be used by a user to achieve a selected result or during an event. Further, it will be understood that the process 146 can be used intra-operatively to alter or create different plans if a selected event occurs. For example, selected events can include accidentally breaching a constraint by a user, unexpected patient response, etc.

The plan can also be displayed as a single plan or the selected single plan on the image data 99 for viewing the user or various users. Further, the plan displayed on the display 36 can include displayed information regarding the plan including catheter size, dosage of a material, and various other information, and an indication of various paths, such as angles, lengths, depths, and the like.

Also, the projected path can be displayed on the image data in block 200. Returning reference to FIG. 6, the projected path can include the dashed line $X_a$ illustrated on the image data 99. The dashed line $X_a$ can be displayed on the display 36 in any appropriate manner, such as in color, in grey scale image, or any other appropriate information. The projected path in block 200 on the image data 99 can be provided for reference by a user or any other path directing instruments, such as a robotic device or the like.

The catheter can also be tracked in block 202. The catheter can be tracked according to any appropriate method, such as an electromagnetic or EM navigation system. As discussed above various tracking sensors can be moved or positioned relative to the catheter 52 to be tracked by the tracking system 44. The tracking sensors 58 can be integrated into the catheter in the appropriate method, such as those disclosed in U.S. patent Ser. No. 11/241,837, filed on Sep. 30, 2005, incorporated herein by reference. It will also be understood that various other tracking methods can be used, such as in a guidable catheter tracking and determining the amount of turning or direction in the amount moved along the selected or directed path. Nevertheless, the catheter 52 can be tracked according to various methods for determining or allowing knowledge of the location of the catheter, particularly a distal tip thereof.

In block 204, an icon representing the catheter, such as a distal tip of the catheter, can be displayed on the image data 99. For example, a differently colored or solid colored region 206 can be displayed on the image data 99 to represent a current location or previous path of the catheter. The indication 206 of the catheter can be displayed relative to the projected path or planned path $X_a$ of the catheter 52 to allow for determining more knowledge of the catheter 52 relative to the projected or planned path $X_a$. This can allow for the provision of feedback regarding the progress or success of the plan in block 206.

The feedback includes various feedback, such as vibration, acoustic signals, visual signals, or the like. For example, the known or tracked path of the catheter 206 can be displayed in a first color, such as green, when the tracked path of the catheter 206 is within a parameter of the plan $X_a$. The parameter relative to the plan $X_a$ can be any appropriate amount, such as a percentage or distance. Nevertheless, if the tracked position of the catheter 206 were to deviate far enough from the planned path $X_a$ the icon or color of the displayed catheter path 208 could change, such as to red. The feedback provided in block 206 can assist the user or the navigation system 10 in assuring that the catheter 52 maintains the paths selected from the proposed plans in block 156. Further, the success of the plan can be displayed on the image data 99, such as indicating a visual indication to stop progress of the catheter 52 or a sound to indicate to a user that the plan selected from the proposed plan 156 has been successfully achieved.

Once the catheter has been positioned appropriately relative to the tumor 170 in the brain 103 the delivery of various materials can be commenced. For example, a particular pharmacological material can be delivered to the catheter relative to the tumor 170 to attempt to achieve various results in the tumor 170, such as degradation thereof.

The display 36 can also display the delivery of the therapy, such as a material to the area, including the tumor 170. For example, various information can be included in the material delivery protocol that includes material absorption in the selected tissue, dispersion time, etc. Therefore, the display 36 can also display a material delivery area 210 as the material is being delivered. This can allow a user to view, in real time, the delivery and dispersion of the material. The display can assist in assuring that an appropriate amount of material is delivered, the proper area is covered by the material, etc.

Thus, the optimized plan can be implemented and tracked to determine the position of the catheter 52 relative to the tumor 170. The tracking system 44, which can be a part of the navigation system 10, can assist in achieving the selected plan from a proposed plan in block 156. The achievement of the optimized plan can be in any appropriate manner, such as positioning the distal end of the catheter 52 in a selected location.

It will be understood that use of the catheter 52 relative to the cranium 17 is merely exemplary in these provided further current discussion. One skilled in the art will understand that various other instruments, anatomical locations, and the like can be used to determine proposed plan in block 156 and be implemented in various manners, such as the navigation implementation in block 192. Further, the various protocols can be altered or changed completely to achieve a selected result in various patients 14.

Further areas of applicability of the present teachings will become apparent from the detailed description provided above. It should be understood that the detailed description and specific examples, while indicating various embodiments, are intended for purposes of illustration only and are not intended to limit the scope of the teachings.

What is claimed is:

1. A method of determining an optimized plan for performing a procedure on a selected patient, comprising:
   acquiring patient specific information of the selected patient;
   selecting a therapy protocol from a plurality of therapy protocols based upon a determined therapy to be applied to the selected patient based at least in part on the acquired patient specific information;
   operating a hardware processor to execute instructions to determine optimized candidate plans based on the selected therapy protocol and the acquired patient specific information;
   wherein the therapy protocol is stored in a computer accessible database,
   wherein the therapy protocol includes optimization criteria, constraints, and search strategies for determining a trajectory for moving an instrument for delivery of a therapy that is based on information acquired from sources other than from the selected patient;
   wherein the patient specific information comprises image data and configurations of the instrument available for the therapy delivery;
   wherein the image data includes a working area;
   wherein the configurations of the instrument include at least one of a turning radius of the instrument, a size of the instrument, a type of the instrument, a shape of the instrument, and a number of instruments;
   wherein the therapy includes a delivery of a material.

2. The method of claim 1, where acquiring patient specific information further includes acquiring image data of the selected patient, acquiring an age of the selected patient, acquiring a gender of the selected patient, acquiring a mass of the selected patient, acquiring a prior medical history of the selected patient, or combinations thereof.

3. The method of claim 1, wherein the therapy protocol includes guidelines for performing the selected therapy; and
   executing a program of instructions with a hardware processor to determine an optimized plan that optimizes the selected therapy protocol for performing the determined therapy in the selected patient based on a combination of the provided patient specific information and the information and criteria stored in the computer accessible database.

4. The method of claim 1, wherein the optimization criteria and constraints includes at least one of selecting a location of interest in the selected patient, selecting a material to be delivered to the location of interest, determining anatomical features to be avoided when providing the therapy to the selected location, selecting the parameters for a position of an instrument relative to the selected location, or combinations thereof.

5. The method of claim 4, further comprising:
   forming the therapy protocol by integrating data from a plurality of related procedures performed on patients other than the selected patient to determine an optimal position of an instrument for performing a therapy within a patient population.

6. The method of claim 5, further comprising:
   accessing optimization criteria and constraints based upon the selected therapy protocol;
   wherein executing the instructions further comprises,
       determining plurality of candidate plans including a path to reach a selected location in the selected patient based upon the accessed optimization criteria and constraints and the provided information relating to the selected patient;
       rating each of the plurality of candidates plan based upon the optimization criteria and constraints; and
       outputting to a human viewable display at least the candidate plan and rating for at least a sub-plurality of the determined plurality of candidate plans; and
   determining a proposed plan by a human user based upon the outputted sub-plurality of candidate plans.

7. The method of claim 5, further comprising:
   processing image data provided as information relating to the selected patient including locating anatomical structures of the patient in the image data, locating a target site in the image data of the patient, locating an entry point for instruments in the image date of the patient, or combinations thereof.

8. The method of claim 7, wherein the processing of the image data is performed by a computer processor to determine at least one of a target location for the selected therapy, a physiological structure in the image data, and an anatomical structure in the image data.

9. The method of claim 8, further comprising:
wherein executing the instructions further comprises determining a candidate plan including a path to reach the target location in the selected patient based upon the accessed optimization criteria and constraints and the provided information relating to the selected patient;
rating the candidate plans based upon the accessed optimization criteria and constraints; and
determining the optimized plan based upon the candidate plans.

10. The method of claim 9, further comprising:
implementing the optimized plan manually, navigated, automatically, or combinations thereof.

11. The method of claim 9, wherein the candidate plans includes determining a plurality of candidate plans;
wherein rating the candidate plans includes determining a candidate plan rating for each of the plurality of candidate plans;
wherein the determined optimized plan is the candidate plan of the plurality of candidate plans with a selected rating and selected by a user from at least a sub-plurality of the plurality of candidate plans; and
performing a therapy on the selected patient based upon the optimized plan based upon the processor executing the program of instructions.

12. The method of claim 10, wherein implementing the optimized plan with navigation includes:
tracking an instrument relative to the selected patient in patient space;
displaying the position of the instrument in image space; and
providing feedback to a user.

13. The method of claim 11, further comprising selecting a selected rating;
wherein selecting the selected rating is performed by a human user.

14. The method of claim 11, wherein the optimization criteria and constraints further includes a selected location of a delivery device relative to a malady of the selected patient, drug delivery rates, a period of drug delivery, or pharmokinetics;
wherein performing a therapy on the selected patient includes delivering a pharmaceutical to the selected patient.

15. The method of claim 12, wherein tracking the instruments in patient space includes tracking the instrument via an acoustic tracking system, an optical tracking system, a radar tracking system, an electromagnetic tracking system, or combinations thereof.

16. The method of claim 12, further comprising:
providing a catheter as the instrument that is to be tracked with tracking sensors relative to a distal end of the catheter;
wherein tracking the instrument includes tracking the catheter by tracking the tracking sensors.

17. A system to determine an optimized therapy for a selected patient, comprising:
a first input system operable to input image data of the selected patient;
a second input system operable to input information regarding the selected patient including an instrument configuration;
a third input system operable to input a recalled and predetermined general therapy protocol including optimization criteria and constraints generated from performing a selected therapy on a population of patients other than the selected patient;
a computer processor unit operable to execute instructions including a search strategy to form a proposed plan based on the inputs from the first input system, the second input system, and the third input system including:
determining a selected location in the image data;
determining an entry point to the selected patient; and
determining a path to reach the selected location from the entry point; and
a therapy delivery system operable to deliver a therapy including a material to the selected patient based upon the proposed plan;
a navigation system including:
a tracking system having a tracking sensor;
an instrument including the tracking sensor to be tracked by the tracking system;
a feedback system operable to provide feedback to a user based upon the tracked position of the instrument relative to the determined path;
a display operable to display an instrument icon representing a location of the instrument relative to the image data displayed on the display and a path icon representing the determined path;
wherein the proposed plan is a patient specific plan for the selected patient;
wherein the display is operable to illustrate a therapy icon illustrating a real time therapy delivery for comparison to the recalled and predetermined general therapy protocol;
wherein the instrument configuration includes at least one of a turning radius of the instrument, a size of the instrument, a type of the instrument, a shape of the instrument, and a number of instruments.

18. The system of claim 17, wherein the instrument is operable to be moved relative to the determined path to reach the selected location;
wherein the instrument icon on the display is operable to display the tracked position of the instrument relative to the path icon illustrating the determined path displayed on the display.

19. The system of claim 17, wherein the second input system includes a keyboard, a touch screen, a mouse, or a memory system, or combinations thereof.

20. The system of claim 17, further comprising:
a robotic manipulation system operable to manipulate an instrument relative to the path determined by the processor.

21. The system of claim 17, wherein the tracking system includes an electromagnetic tracking system including a coil array operable to transmit signals, wherein the tracking sensor is operable to receive and transmit signals based upon the signals transmitted by the coil array.

22. The system of claim 17, wherein the first input system includes an imaging system operable to image the selected patient to form the image data.

23. The system of claim 17, wherein the instructions further include constraints that must be met by the proposed plan to have the proposed plan perform a procedure on the selected target including identified anatomical features, clearance distances of the identified anatomical features, prior procedures of the selected patient, or combinations thereof.

24. The system of claim 21, further comprising:
a dynamic reference frame positioned relative to the selected patient and operable to assist the navigation system in maintaining a registration between a patient space of the selected patient and an image space of the image data.

25. The system of claim 22, wherein the imaging system includes at least one of an MRI, an SPECT, a PGS, a CT scanner, an x-ray system, a PET, or combinations thereof.

26. The system of claim 22, wherein the imaging system includes a first imaging system to provide image data of a first type and a second imaging system operable to provide image data of a second type;
wherein the first input system is operable to form a composite image data of the first image data type and the second image data type;
whereby an image computer processor unit is operable to identify at least one selected location in the image data of the first type or the composite image data.

27. The system of claim 23, wherein the processor is operable to execute instructions based upon a delivery protocol included as a part of the general therapy protocol for a therapy.

28. The system of claim 27, further comprising:
a human viewable output display to display a plurality of proposed plans and an associated plan goodness value to each of the displayed plurality of proposed plans;
wherein the delivery protocol is operable to provide both constraints which cannot be breached and optimization criteria to assist in determining a proposed plan that has a higher plan goodness value than a plurality of candidate plans.

29. The system of claim 27, wherein the determination of a proposed plan includes determining a path in a exhaustive method.

30. A method to determine an optimization of a selected therapy for a selected patient, comprising:
inputting patient specific image data of the selected patient;
inputting non-image patient specific information regarding the selected patient different than the input patient specific image data;
selecting a general therapy based at least in part on the input patient specific image data of the selected patient and the input non-image patient specific information regarding the selected patient different than the input patient specific image data;
recalling from a memory system a general therapy protocol including specific guidelines for performing the selected general therapy based on performing the selected therapy on a population of patients other than the selected patient, wherein the specific guidelines include at least one of an optimization criteria and a constraint criteria; and
executing instructions including a search strategy with a computer processor to form a proposed optimized plan based on the input patient specific image data, the input non-image patient specific information, and the recalled general therapy protocol, wherein executing the instructions includes:
determining a selected working area in the image data;
determining an entry point to the selected patient; and
determining a path to reach the selected working area from the determined entry point;
wherein the proposed optimized plan is a patient specific plan for the selected patient;
wherein the inputted non-image patient specific information includes at least one of a turning radius of the instrument, a size of the instrument, a type of the instrument, a shape of the instrument, and a number of instruments;
wherein the selected therapy includes a delivery of a material.

31. The method of claim 30, wherein the constraint criteria must be met by the proposed optimized plan including identified anatomical features, clearance distances of the identified anatomical features, prior procedures of the selected patient, or combinations thereof.

32. The method of claim 31, further comprising:
delivering a drug with a drug delivery system to the selected patient based upon the proposed plan;
navigating an instrument based on the proposed plan at least by tracking the instrument with a tracking sensor associated with the instrument;
receiving feedback based upon the tracked position of the instrument relative to the determined path;
displaying an instrument icon, a path icon, the input patient specific image data, and a therapy icon;
wherein the instrument icon is illustrated relative to both the path icon and the input patient specific image data to represent a location of the instrument relative to the image data and the path icon representing the determined path;
wherein the therapy icon illustrates a real time therapy delivery for comparison to the recalled general therapy protocol.

33. The method of claim 32, further comprising:
wherein executing the program further comprises,
determining plurality of candidate plans including a path to reach a selected location in the selected patient based upon the optimization criteria and a constraint criteria and the input patient specific image data of the selected patient and the input non-image patient specific information regarding the selected patient different than the input patient specific image data;
rating each of the determined plurality of candidate plans based upon the optimization criteria and a constraint criteria; and
outputting to a human viewable display at least the candidate plan and rating for a sub-plurality of the determined plurality of candidate plans; and
selecting the proposed plan by a human user from the outputted sub-plurality of candidate plans.

34. A method of automatically determining an optimized therapy for a selected patient based upon general therapy protocols and patient specific information, comprising:
selecting a general therapy to be applied to the selected patient to treat a malady of the selected patient;
instructing a processor to recall a stored general therapy protocol relating to performing the selected general therapy to treat the malady, wherein the general therapy protocol is stored in a computer accessible storage system and includes optimization criteria and constraints based on integrating data from previously performed selected therapies to treat the malady in previous patients other than the selected patient;
instructing the processor to recall image data of the selected patient;
inputting an instrument configuration of an instrument including at least one of a turning radius of the instrument, a size of the instrument, a type of the instrument, a shape of the instrument, and a number of instruments;
inputting a therapy material information;
selecting a candidate plan that includes a trajectory for the instrument that was outputted by the processor, where the trajectory is determined with search strategies based upon the recalled general therapy protocol and the recalled image data to determine an optimal plan of therapy for the selected patient; and
moving an instrument based upon the determined plan.

35. The method of claim 34, wherein the optimization criteria includes criteria that can be weighted to provide a plan goodness value for determining the optimal plan in the selected patient based upon the general therapy protocol.

36. The method of claim 34, wherein the selected candidate plan includes determining the highest plan goodness value of a plurality of determined candidate plans that are found during a search of the accessed image data of the selected patient based upon the general therapy protocol.

37. The method of claim 34, wherein recalling a general therapy protocol includes accessing previously collected information relating to a standard therapy procedure protocol and accessing previously collected information relating to the therapy material type.

38. The method of claim 36, further comprising:
delivering a pharmaceutical to the selected patient based upon the selected plan;
wherein the accessed general therapy protocol includes a selected location of a delivery device relative to a malady of the selected patient, drug delivery rates, a period of drug delivery, or pharmokinetics.

39. The method of claim 37, wherein the recalled general therapy protocol can include pharmacokinetics, drug delivery rates, drug toxicity, drug interactions, delivery devices, optimal position of a delivery device, portions of the anatomy of a patient in a patient population to be avoided, or combinations thereof.

40. The method of claim 37, further comprising:
providing an image pre-processor operable to process the image data of the selected patient.

41. The method of claim 37, further comprising:
searching the recalled image data of the selected patient based upon the accessed general therapy protocol to form a candidate plan; and
wherein determining a candidate plan includes applying an optimization criteria and a constraint to determine a plan goodness value of the candidate plan.

42. The method of claim 39, further comprising:
inputting patient specific information of the selected patient to be used by the processor executing a program to determine the candidate plan;
wherein the patient specific information includes sex, mass, age, prior medical history, volume, or combinations thereof.

43. The method of claim 40, further comprising:
pre-processing the image data of the selected patient with the provided image pre-processor, wherein the image pre-processor includes a computer processor system operable to execute instructions to identify anatomical structures, identify anatomical surfaces, identify target locations, or combinations thereof.

44. The method of claim 41, further comprising:
outputting a plurality of the candidate plans based upon the search of the image data.

45. The method of claim 43, wherein moving an instrument includes moving the instrument from an entry point to the identified target location based upon the optimal plan.

46. The method of claim 44, further comprising:
selecting by a human user the optimal plan based upon the plan goodness value of the outputted plurality of the candidate plans.

47. The method of claim 46, wherein the optimal plan includes at least an entry point, a target location, and a path to be followed when moving the instrument.

48. The method of claim 47, further comprising:
tracking the instrument with a navigation system;
displaying the image data on a display; and
displaying an icon representing the location of the instrument relative to the image data of the selected patient.

* * * * *